US012728180B1

(12) United States Patent
Alkhuriji et al.

(10) Patent No.: US 12,728,180 B1
(45) Date of Patent: Sep. 8, 2026

(54) GUM OLIBANUM NANOFIBERS FOR DRUG RELEASE AND WOUND HEALING APPLICATIONS

(71) Applicant: KING SAUD UNIVERSITY, Riyadh (SA)

(72) Inventors: Afrah Fahad Alkhuriji, Riyadh (SA); Manal Ahmed Awad, Riyadh (SA); Khalid Mustafa Ortashi, Riyadh (SA); Mohamed Hassan Elnewehy, Riyadh (SA); Abdullah Mussad Alenizi, Riyadh (SA); Hayat Saeed Althobaiti, Riyadh (SA); Meera Moydeen Abdulhameed, Riyadh (SA); Hamad Ahmed Al Salman, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 19/436,064

(22) Filed: Dec. 30, 2025

(51) Int. Cl.

| | |
|---|---|
| ***A61L 15/22*** | (2006.01) |
| ***A61L 15/44*** | (2006.01) |
| ***C08L 29/04*** | (2006.01) |
| ***C08L 93/00*** | (2006.01) |
| ***D01D 5/00*** | (2006.01) |

(52) U.S. Cl.
CPC ............. *A61L 15/225* (2013.01); *A61L 15/44* (2013.01); *C08L 29/04* (2013.01); *C08L 93/00* (2013.01); *D01D 5/003* (2013.01); *A61L 2300/624* (2013.01); *A61L 2430/34* (2013.01); *D10B 2321/08* (2013.01)

(58) Field of Classification Search
CPC ....... A61L 15/225; C08L 29/04; D01D 5/003; D10B 2321/08
See application file for complete search history.

(56) References Cited

U.S. PATENT DOCUMENTS

| | | | | |
|---|---|---|---|---|
| 12,098,479 | B2 | 9/2024 | Hou et al. | |
| 12,194,191 | B1 | 1/2025 | Awad et al. | |
| 2015/0030708 | A1 * | 1/2015 | Chamberland | A61L 15/40 424/744 |
| 2023/0120697 | A1 * | 4/2023 | Soane | C08L 89/06 424/443 |

FOREIGN PATENT DOCUMENTS

| | | | | |
|---|---|---|---|---|
| CN | 116941834 | A | 10/2023 | |
| CN | 117587578 | A * | 2/2024 | D04H 1/728 |
| CN | 115807334 | B | 7/2024 | |

OTHER PUBLICATIONS

El-Newehy, M. H., et al., "Single-nozzle Core-shell Electrospun Nanofibers of PVP/Dextran as Drug Delivery System," Fibers and Polymers, 20(10): pp. 2078-2089 (2019)).
Daliri, Ava, et al. "Chemical modification of frankincense gum and its application in nano-fibers containing peppermint essential oil/ modified frankincense gum/zein." Journal of Food Measurement and Characterization 18.6 (2024): 4288-4300. Abstract.

* cited by examiner

*Primary Examiner* — Susan T Tran
*Assistant Examiner* — William Craigo
(74) *Attorney, Agent, or Firm* — Nath, Goldberg & Meyer; Joshua B. Goldberg

(57) ABSTRACT

Methods of making gum olibanum nanofibers and *Acacia nilotica* nanoparticle loaded gum olibanum nanofibers (composite nanofibers) are provided. The methods include mixing gum olibanum with acetic acid, adding water, stirring, adding polyvinyl alcohol, and electrospinning to obtain the gum olibanum nanofibers. A solution of *Acacia nilotica* nanoparticles may be mixed with the gum olibanum nanofibers, prior to a further round of electrospinning to obtain composite nanofibers. The gum olibanum nanofibers and the composite nanofibers may be used for controlled drug release applications or for wound healing applications.

17 Claims, 21 Drawing Sheets

GUM OLIBANUM NANOFIBERS FOR DRUG RELEASE AND WOUND HEALING APPLICATIONS

FIELD AND BACKGROUND OF THE INVENTION

The disclosure of the present patent application relates to nanotechnology, and particularly to gum olibanum nanofibers for drug release and wound healing applications.

DESCRIPTION OF THE PRIOR ART

Green nanofiber-based materials have emerged as a promising solution for biomedical applications, offering eco-friendly, biocompatible, and highly functional properties. These advanced nanofibers play a crucial role in wound healing and drug delivery, providing an effective platform for controlled drug release, enhanced tissue regeneration, and infection prevention. By incorporating sustainable production methods with innovative nanotechnology, green nanofiber scaffolds hold great potential for applications in bandages, wound dressings, therapeutic pads, hemostatic textiles, and antibacterial clothing. This cutting-edge approach has the potential to address critical healthcare challenges and promote sustainability in biomedical material development. However, specific products delivering on the wide-ranging potential of green nanofiber-based materials must still be developed.

Thus, gum olibanum nanofibers for drug release and wound healing applications solving the aforementioned problems are desired.

SUMMARY OF THE INVENTION

The present methods may include obtaining a quantity of gum olibanum, adding the quantity of gum olibanum to acetic acid to obtain a first mixture, and mixing the first mixture. Subsequently, either distilled or deionized water may be added to the first mixture to obtain a second mixture. The second mixture may then be continuously stirred at a speed of about 500-1000 rpm and heated to about 85-90° C. until a clear, milky solution forms. An about 10 wt % aqueous solution of polyvinyl alcohol ("PVA") may be prepared as a blending agent by stirring a mixture of polyvinyl alcohol and water for about 10-12 hours at about 85-90° C. The clear, milky solution and the about 10 wt % aqueous solution of PVA may be combined in an equal volume ratio to obtain a third mixture. The third mixture may be stirred at a low speed (about 100 rpm) for about 5 hours to ensure thorough mixing and then roo898uested at room temperature for about 24 hours. The third mixture may then be electrospun to produce gum olibanum nanofibers.

In some embodiments, the gum olibanum nanofibers may be loaded with *Acacia nilotica* nanoparticles. First, *Acacia nilotica* plant material with its husks may be washed, air-dried, and then ground using an electric grinder to obtain ground *Acacia nilotica* plant material. The ground *Acacia nilotica* plant material may be sieved and the resulting fine powder ("powdered *Acacia nilotica* plant material") may be stored for further use. Next, the powdered *Acacia nilotica* plant material may be dissolved in methanol and then sprayed dropwise into boiling water under a first set of ultrasonic conditions to obtain a first solution. The first solution may be stirred at a controlled temperature (about 30-35° C.) to form *Acacia nilotica* nanoparticles within the first solution. In some embodiments, the first solution including *Acacia nilotica* nanoparticles may be dried to form an *Acacia nilotica* nanoparticle powder.

The present gum olibanum nanofibers loaded with *Acacia nilotica* nanoparticles may be synthesized by adding the solution including *Acacia nilotica* nanoparticles (or resuspending the *Acacia nilotica* nanoparticles in a solution and then adding that solution) slowly to the presently disclosed gum olibanum nanofibers under a second set of ultrasonic conditions to obtain a second solution. The second solution may then be electrospun to produce the gum olibanum nanofibers loaded with *Acacia nilotica* nanoparticles ("composite nanofibers").

In certain embodiments, the present nanofibers include gum olibanum nanofibers prepared according to the present methods. In other embodiments, the present nanofibers include gum olibanum nanofibers loaded with *Acacia nilotica* nanoparticles prepared according to the present methods.

In certain embodiments, the present nanofibers may be used for controlled drug release or for wound healing applications.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
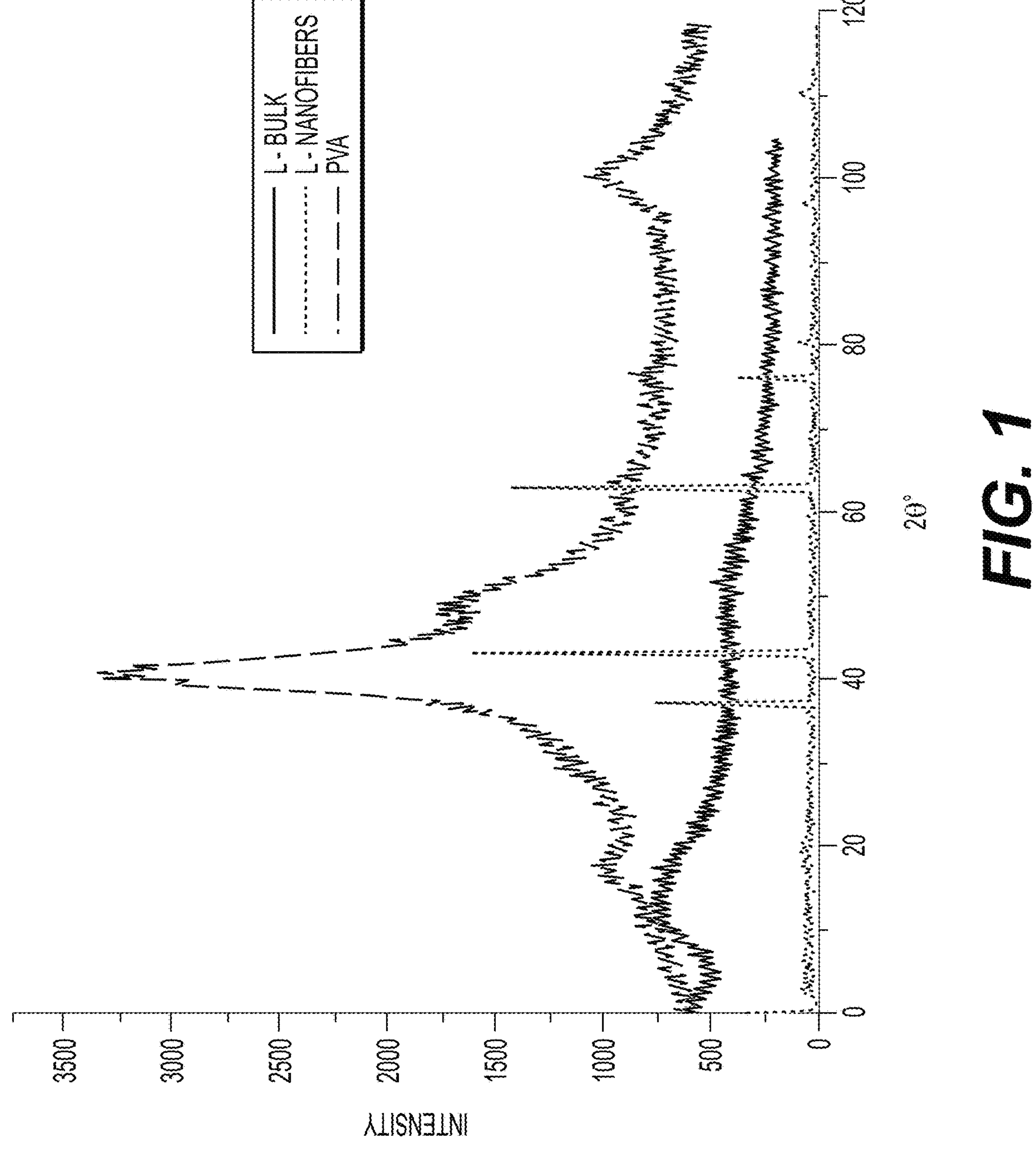
FIG. 1 depicts the XRD diffraction patterns of a sample of raw gum Olibanum ("L-bulk"), a sample of gum olibanum nanofibers ("L-nanofibers"), and PVA.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as Diabetes.

As used herein, "gum olibanum" refers to an aromatic resin obtained from trees of the genus *Boswellia* in the family Burseraceae and commonly called "Frankincense".

As used herein "*Acacia nilotica*" refers to a flowering tree in the family Fabaceae that is native to Africa, the Middle East, and the Indian subcontinent and that is also known as "*Vachellia nilotica*", "gum Arabic tree", "babul", "thorn mimosa", "Egyptian acacia", or "thorny acacia".

The present methods may include obtaining a quantity of gum olibanum, adding the quantity of gum olibanum to acetic acid to obtain a first mixture, and mixing the first mixture. Subsequently, either distilled or deionized water may be added to the first mixture to obtain a second mixture. The second mixture may then be continuously stirred at a speed of about 500-1000 rpm and heated to about 85-90° C. until a clear, milky solution forms. An about 10 wt % aqueous solution of polyvinyl alcohol ("PVA") may be prepared as a blending agent by stirring a mixture of polyvinyl alcohol and water for about 10-12 hours at about 85-90° C. The clear, milky solution and the about 10 wt % aqueous solution of PVA may be combined in an equal volume ratio to obtain a third mixture. The third mixture may be stirred at a low speed (about 100 rpm) for about 5 hours to ensure thorough mixing and then rested at room temperature for about 24 hours. The third mixture may then be electrospun to produce gum olibanum nanofibers.

In an embodiment, the quantity of gum olibanum may be about 15 g and it may be added to about 5 mL of acetic acid. The quantity of deionized water added to the first mixture may be about 100 mL.

In an embodiment, the gum olibanum may be obtained from a *Boswellia sacra* tree.

In an embodiment, electrospinning the third mixture may include filling a syringe with the third mixture and attaching the syringe to an electrospinning machine; applying a voltage of about 15 kV with a distance of about 15 cm maintained between the collector and the syringe tip; and collecting gum olibanum nanofibers on the collector of the electrospinning machine. The resultant gum olibanum nanofibers may then be dried in an oven at about 120° C. for about 6 hours to remove any residual solvent.

In some embodiments, the gum olibanum nanofibers may be loaded with *Acacia nilotica* nanoparticles. First, *Acacia nilotica* plant material with its husks may be washed, air-dried, and then ground using an electric grinder to obtain ground *Acacia nilotica* plant material. The ground *Acacia nilotica* plant material may be sieved and the resulting fine powder ("powdered *Acacia nilotica* plant material") may be stored for further use. Next, the powdered *Acacia nilotica* plant material may be dissolved in methanol and then sprayed dropwise into boiling water under a first set of ultrasonic conditions to obtain a first solution. The first solution may be stirred at a controlled temperature (about 30-35° C.) to form *Acacia nilotica* nanoparticles within the first solution. In some embodiments, the first solution including *Acacia nilotica* nanoparticles may be dried to form an *Acacia nilotica* nanoparticle powder.

In an embodiment, the *Acacia nilotica* plant material used to make the *Acacia nilotica* nanoparticles may include about 20 grams of *Acacia nilotica* plant material.

In an embodiment, sieving the ground *Acacia nilotica* plant material may include passing the plant material through a 200 mesh nylon sieve with 75 μm apertures. The retained fraction (>75 μm) may be discarded and the passing fraction, having a size ≤75 μm, may be designated as the resulting fine powder that is stored for future use.

In an embodiment, about 0.5 g of the fine powder may be dissolved in about 10 mL of the methanol and sprayed dropwise into about 50 ml of the boiling water at a flow rate of about 0.5 mL/min over about 5 minutes. The first set of ultrasonic conditions may be about 750 W power and about 20 kHz frequency and may be maintained for about 20-23 minutes.

The present gum olibanum nanofibers loaded with *Acacia nilotica* nanoparticles may be synthesized by adding the solution including *Acacia nilotica* nanoparticles (or resuspending the *Acacia nilotica* nanoparticles in a solution and then adding that solution) slowly to the presently disclosed gum olibanum nanofibers under a second set of ultrasonic conditions to obtain a second solution. The second solution may then be electrospun to produce the gum olibanum nanofibers loaded with *Acacia nilotica* nanoparticles ("composite nanofibers").

In an embodiment, the second set of ultrasonic conditions may include about 750 W power and about 20 kHz frequency for about 3 hours.

In an embodiment, electrospinning the second solution may include filling a syringe with the second solution and attaching the syringe to an electrospinning machine. A voltage of about 15 kV may be applied, with an about 15 cm distance maintained between the collector and the syringe tip. Upon voltage application, composite nanofibers may be generated and collected on the collector. The resultant composite nanofibers may be dried in an oven at about 120° C. for about 6 hours to remove any residual solvent.

In certain embodiments, the present nanofibers include gum olibanum nanofibers prepared according to the present methods. In other embodiments, the present nanofibers include gum olibanum nanofibers loaded with *Acacia nilotica* nanoparticles prepared according to the present methods.

In certain embodiments, the present nanofibers may be used for controlled drug release. In these embodiments, the present nanofibers may be loaded with a drug or biologically active agent of interest using any method generally known in the art. In some embodiments, the drug loaded nanofibers may be gum olibanum nanofibers. In further embodiments, the drug loaded nanofibers may be gum olibanum nanofibers loaded with *Acacia nilotica* nanoparticles. In some embodiments, the drug loaded on the present nanofibers may be ciprofloxacin.

In certain embodiments, the present nanofibers may be used for wound healing applications. The present nanofibers may be administered to a wound site on a subject in need thereof. In some embodiments, the nanofibers may be affixed to the wound site on the subject using a bandage. In other embodiments, the nanofibers may be loaded into or onto a bandage, gel, wrap, wound dressing, or therapeutic pad, or any other wound healing device now known or later developed. In some embodiments, the nanofibers may be incorporated into a hemostatic textile or antibacterial clothing. In some embodiments, the nanofibers may be gum olibanum nanofibers. In further embodiments, the nanofibers may be gum olibanum nanofibers loaded with *Acacia nilotica* nanoparticles. In some embodiments, the nanofibers may be loaded with one or more drugs of interest, including but not limited to an antibiotic, analgesic, or other drug known to be useful for wound healing applications. In some embodiments, the drug may be ciprofloxacin. In some embodiments, the wounds may be diabetic wounds.

The present compositions and methods may be better understood in view of the following examples.

Example 1

Synthesis of a Gum Olibanum Nanofiber Solution

A 15 g portion of gum olibanum (also known as frankincense) obtained from the *Boswellia sacra* tree was added to 5 mL of acetic acid and mixed thoroughly using a spatula to obtain a first mixture. Subsequently, 100 mL of distilled or deionized water was added to the first mixture to obtain a second mixture. The second mixture was continuously stirred at a speed of 500-1000 rpm and heated to 85-90° C. until a clear, milky solution was formed. A 10 wt % aqueous solution of polyvinyl alcohol (PVA) was prepared as a blending agent by stirring a mixture of polyvinyl alcohol and water for 10-12 hours at 85-90° C. Afterward, the clear, milky solution and the aqueous solution were combined in an equal volume ratio to obtain a third mixture. The third mixture was stirred at a low speed (100 rpm) for 5 hours to ensure thorough mixing and then left to rest at room temperature for 24 hours. A syringe was filled with the third mixture and attached to an electrospinning machine. A voltage of 15 kV was applied, with a distance of 15 cm maintained between the collector and the syringe tip. Upon application of the voltage, gum olibanum nanofibers were generated and collected on the collector. The resultant olibanum nanofibers were dried in an oven at 120° C. for 6 hours to remove any residual solvent.

Example 2

Synthesis of a Gum Olibanum and *Acacia nilotica* Composite Nanofiber Solution

First, 20 grams of *Acacia nilotica* plant material with its husks were thoroughly washed under running tap water, air-dried, and then ground using an electric grinder. The ground material was sieved through a 200 mesh nylon sieve with 75 μm apertures and the passing fraction, having a size ≤75 μm, and the resulting fine powder was stored for further use. Next, 0.5 g of *Acacia nilotica* powder was dissolved in approximately 10 mL of methanol and then sprayed dropwise into 50 mL of boiling water at a flow rate of 0.5 mL/min over 5 minutes under ultrasonic conditions (750 W power, 20 kHz frequency) for 20-30 minutes to obtain a first solution. The first solution was stirred at a controlled temperature (30-35° C.) to obtain an *Acacia nilotica* nanoparticle solution.

A gum olibanum/*Acacia nilotica* composite nanofiber solution was then synthesized by adding the solution of *Acacia nilotica* nanoparticles slowly to the olibanum nanofibers prepared according to Example 1 under ultrasonic conditions (750 W power, 20 KHz frequency) for 3 hours.

A syringe was filled with the Gum Olibanum/*Acacia nilotica* composite nanofiber solution and attached to an electrospinning machine. A voltage of 15 kV was applied, with a 15 cm distance maintained between the collector and the syringe tip. Upon voltage application, composite nanofibers were generated and collected on the collector. The resultant composite nanofibers were dried in an oven at 120° C. for 6 hours to remove any residual solvent.

Example 3

Using Gum Olibanum Nanofibers for Controlled Drug Release

The mechanism of drug release and its kinetics were assessed in a drug delivery system. Mathematical models of drug release were used as a valuable instruments for preclinical formulation optimization. These mathematical models also offer insights into the mechanisms that regulate drug release. Multiple mathematical models must be utilized to ascertain the appropriate drug release mechanism, taking into consideration drug transport from polymer matrices, the polymer's physical structure, water diffusion, drug characteristics and solubility, as well as the inherent interactions between the polymer and the drug. In this study, non-linear kinetic models such as the First order, Korsmeyer-Peppas, Higuchi, and Weibull models (Equations 1-4) were applied to the experimental data, in order to evaluate the drug release mechanism for the drug encapsulated nanofiber mats.

The equations for the abovementioned models are as follows:

Korsmeyer-Peppas — Equation 1

$$F = K_{kp}t^n$$

In Equation 1, F is the fraction of the drug released at time t; $K_{kp}$ is the release constant, which includes the geometric and structural characteristics of the drug-dosage form; and n is the diffusional exponent, which indicates the drug-release mechanism.

The First Order Kinetic Model — Equation 2

$$F = 1 - e^{-K_1 t}$$

In Equation 2, $K_1$ is the first order constant and F is the fraction of the drug released at time t.

The Weibull Model — Equation 3

$$F = \left(1 - e^{-at^b}\right)$$

In equation 3, a and b are constants that describe the drug-release profile and F is the fraction of the drug released at time t.

The Higuchi Model — Equation 4

$$F = K_{HC}t^{1/2}$$

In equation 4, $K_{HC}$ is the Higuchi constant and Fis the fraction of the drug released at time t.

Nonlinear trial-and-error procedures were employed with the Origin Lab software to determine the parameters of the kinetic models. The coefficient of determination ($R^2$) and chi-square ($\chi^2$) for the non-linear optimization approach were computed using Equations (4) and (5). The optimal model for elucidating the drug release mechanism was determined based on the values of R2 and χ2

$$\chi^2 = \sum_i \frac{(F_{exp} - F_{cal})^2}{F_{cal}} \quad \text{Equation 5}$$

$$R^2 = 1 - \frac{\sum_i (F_{exp} - F_{cal})^2}{\sum_i (F_{exp} - F_{mean})^2} \quad \text{Equation 6}$$

In Equations 5 and 6, $F_{exp}$ is the fraction of the drug released at time t, $F_{cal}$ is the fraction of the drug released, which was obtained from the model after using the Origin Lab program, and $F_{mean}$ is the mean of the $F_{exp}$ values.

The total drug loaded onto olibanum nanofiber mats was analyzed as reported previously by El-Newehy et al. (El-Newehy, M. H., et al., "Single-nozzle Core-shell Electrospun Nanofibers of PVP/Dextran as Drug Delivery System,"

Fibers and Polymers, 20 (10): pp. 2078-2089 (2019)) Briefly, a known weight of drug loaded nanofiber was dipped in 10 mL of PBS buffer (pH 9.2) and heated to 60° C. The absorbance was measured by UV spectrophotometer at 276 nm. The measurement was repeated until a constant value was obtained. The drug encapsulation efficiency was then calculated using Equation 7.

$$\text{Encapsulation Efficiency (\%)} = \left(\frac{\text{Encapsulated drug}}{\text{Total drug added}}\right) \times 100 \quad \text{Equation 7}$$

Figure 9:
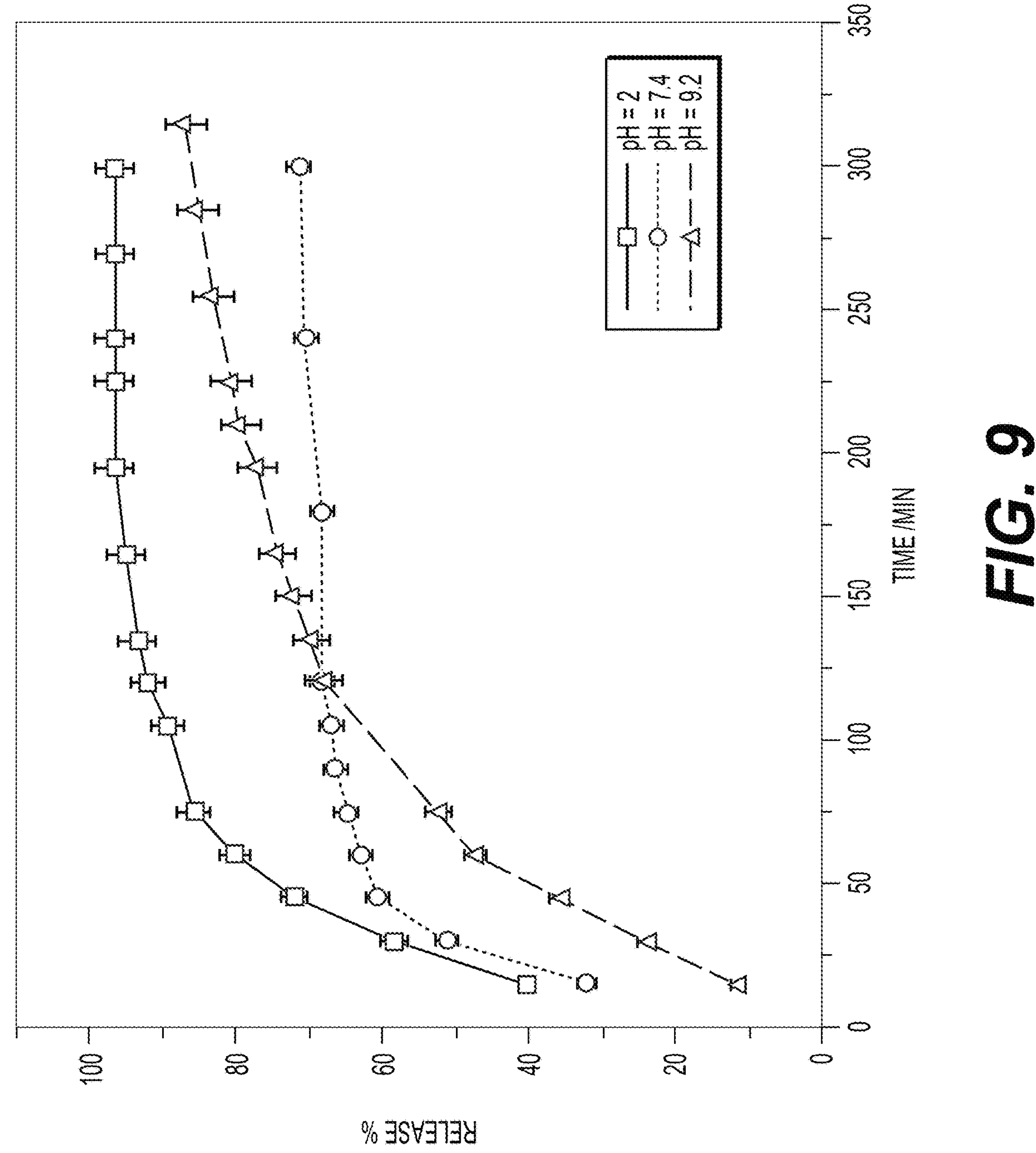
FIG. 9 depicts the cumulative precent release of ciprofloxacin from gum olibanum nanofibers as a function of time under specific pH conditions.

The drug release behavior of olibanum nanofiber was analyzed by the same method. The cumulative percent release of ciprofloxacin from nanofibers as a function of time is shown in FIG. 9. The drug-loaded nanofibers showed an initial burst release within 30 minutes around 58% at pH=2, 51% at pH=7.4 and 21% at pH 9.2. The initial burst release may have occurred due to the drug being present on the surface of the nanofiber. The initial burst release was followed by sustained release behavior over 5 hours. In acidic pH, almost 96% of the drug was released into the medium which may have resulted from diffusion and polymer erosion due to the acidic medium. Sustained and slow release was achieved at pH=7.4 by diffusion of drug from the polymer matrix into the medium. At pH=9.2, sustained release was observed and 90% of the drug was released within 5 hours.

Figure 10A:
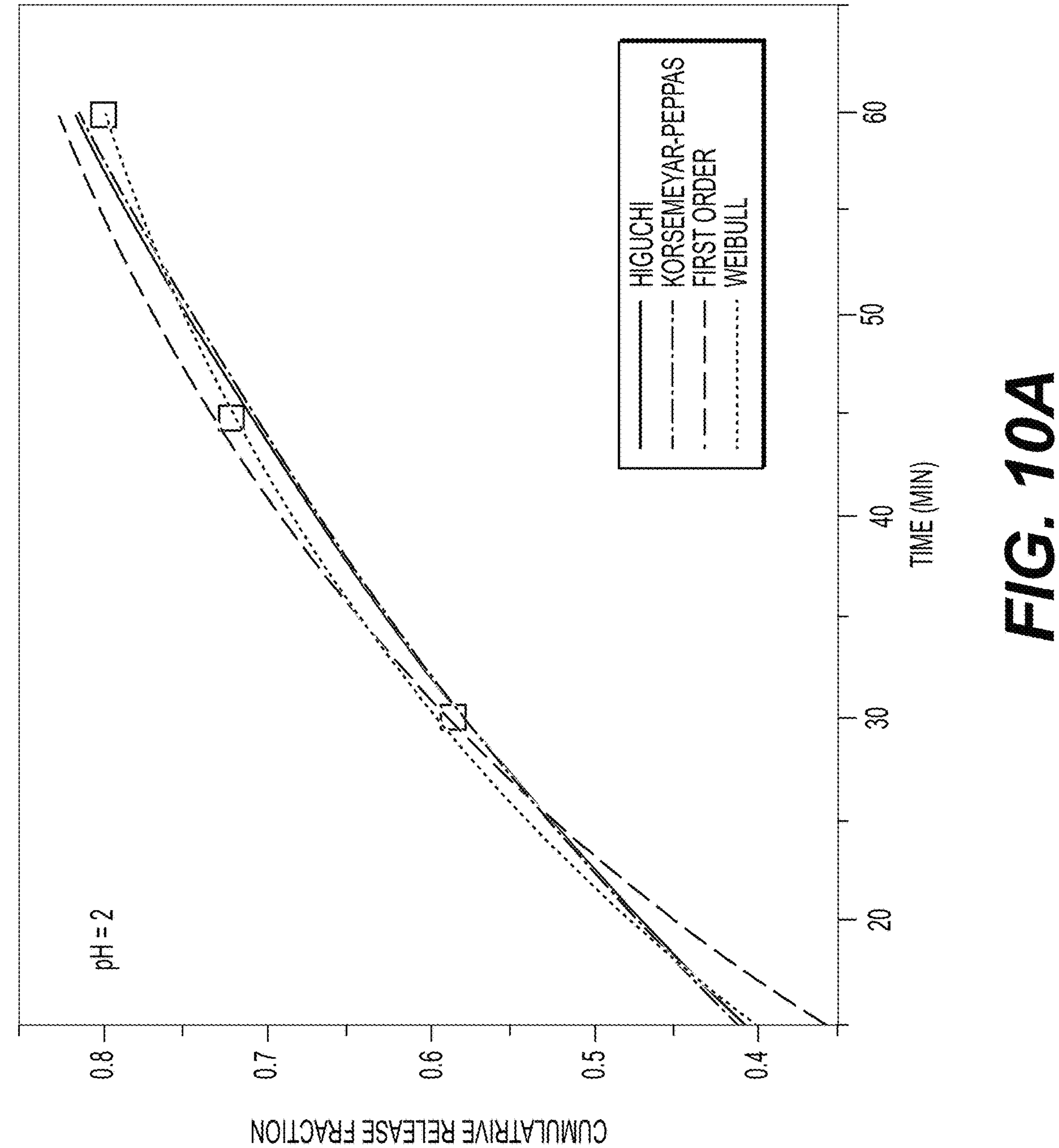
FIGS. 10A-10C depict non-linear kinetic studies of drug release from gum olibanum nanofibers at pH 2 (FIG. 10A), pH 7.4 (FIG. 10B) and pH 9.2 (FIG. 10C).
Figure 10B:
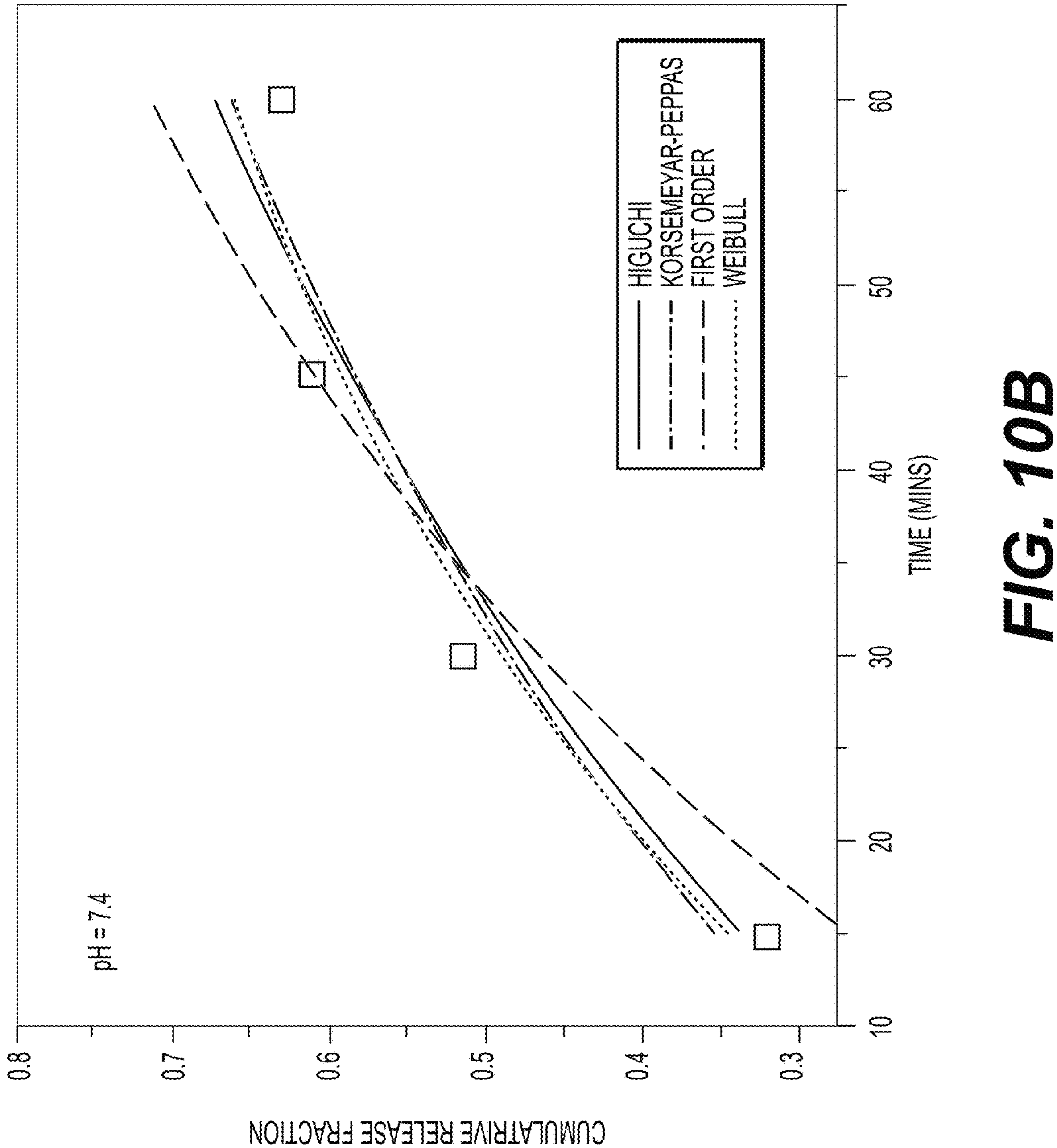
Figure 10C:
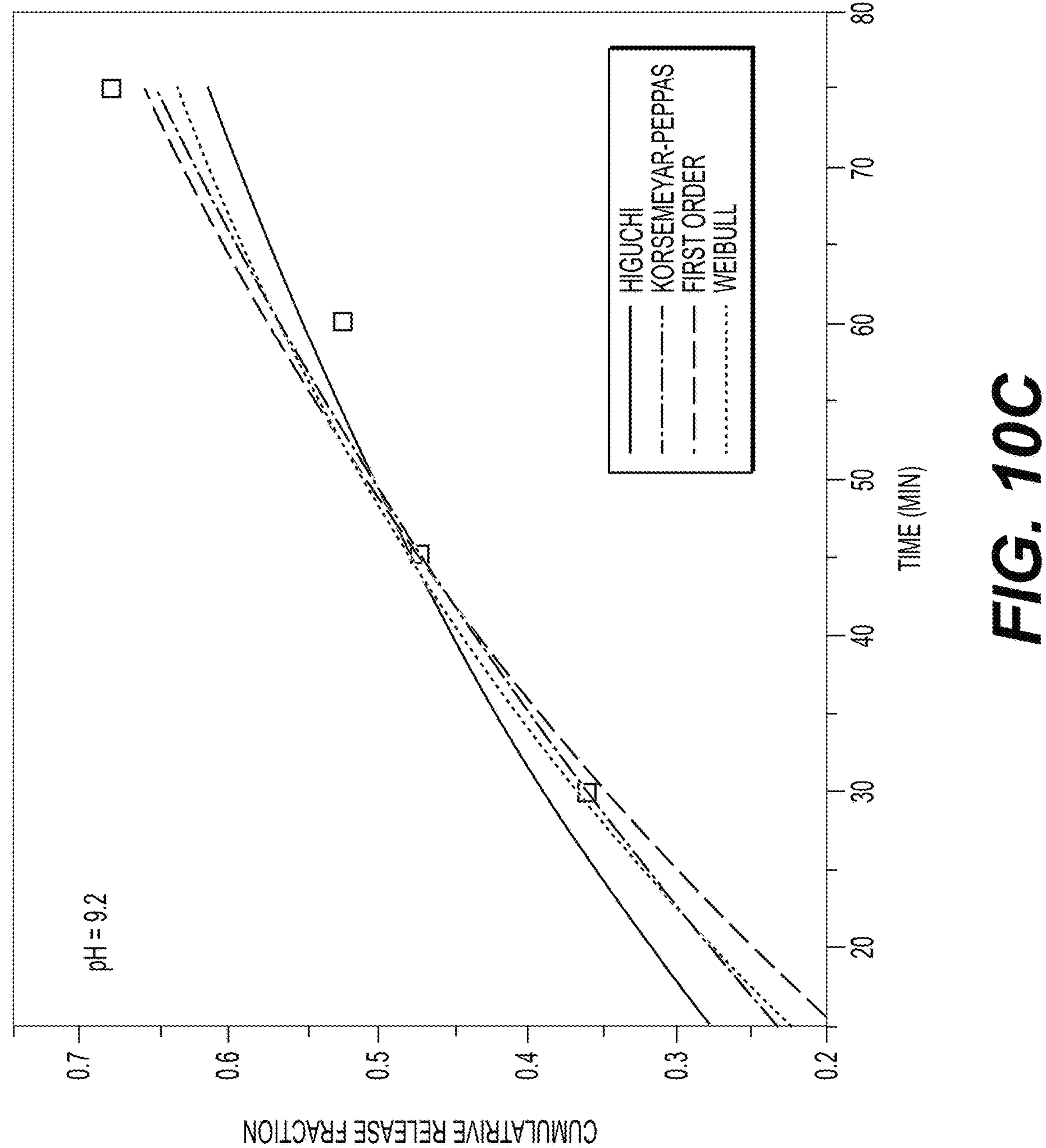

The kinetic models used in the study were Korsmeyer-Peppas, Weibull, Higuchi, and the First Order Kinetic Model. These models were applied for the estimation of the respective equations of Ciprofloxacin-loaded PVA blend nanofibers by non-linear fitting. The first 60 minutes of drug release was selected for this kinetic study. The results obtained from the kinetic models are presented in Table 1 and FIGS. 10A-10C. In the Korsmeyer-Peppas model, the value of n<0.45 in case of pH=7.4, indicated that drug release mechanism depended on Fickian diffusion or quasi-Fickian diffusion. In pH 2 and pH 9.2, the n values were found to be in the range of 0.45 and 1, suggesting anomalous diffusion. In the Weibull model, the b coefficient values were correlated with the mechanism of drug release throughout the polymer matrix. The b value for pH=7.4 were in the range of 0.39-0.69, confirming the mechanism of drug release to be diffusion in disordered or fractal substrate in which the morphology differed from percolation cluster (Table 1). The b values for pH=2 and pH=9.2 were found to be in the range of 0.75 and 1, suggesting diffusion in normal Euclidian space with another release mechanism. The best fit model for all pH was found to be Weibull model according to the $R^2$ and $\chi 2$ values.

TABLE 1

Kinetic Study Results

| Kinetic Model | pH = 2 | pH = 7.4 | pH = 9.2 |
|---|---|---|---|
| Korsemeyar-Peppas | | | |
| k | 0.10946 ± 0.01211 | 0.1018 ± 0.0356 | 0.04039 ± 0.0106 |
| n | 0.49039 ± 0.02934 | 0.4573 ± 0.09309 | 0.64368 ± 0.06518 |
| $R^2$ | 0.99416 | 0.93751 | 0.97742 |
| $\chi^2$ | 2.6799E−4 | 0.00188 | 8.20879E−4 |
| Higuchi | | | |
| k | 0.10663 ± 0.00112 | 0.08681 ± 0.00304 | 0.07115 ± 0.00271 |
| $R^2$ | 0.99385 | 0.93079 | 0.93961 |
| $\chi^2$ | 1.88099E−4 | 0.00139 | 0.00165 |
| Weibull | | | |
| k | 0.05329 ± 0.00423 | 0.06558 ± 0.02576 | 0.02408 ± 0.01068 |
| n | 0.83306 ± 0.02224 | 0.68355 ± 0.10786 | 0.86576 ± 0.11344 |
| $R^2$ | 0.99887 | 0.96044 | 0.96349 |
| $\chi^2$ | 5.2048E−5 | 0.00119 | 0.001033 |
| First Order | | | |
| k | 0.02954 ± 0.00141 | 0.02076 ± 0.002 | 0.01428 ± 7.70672E−4 |
| $R^2$ | 0.9681 | 0.80268 | 0.94796 |
| $\chi^2$ | 9.7610E−4 | 0.00396 | 9.7610E−4 |

Example 3

Using Gum Olibanum Nanofibers for Wound Healing

30 Wistar albino male rats (200 g±30, 8-10 weeks old) were obtained from King Saud University in Riyadh, Saudi Arabia. The animals were housed in polycarbonate cages at 25±2° C. and 55-60% humidity under a 12-hr light/dark cycle.

To induce a model of Type 2 Diabetes Mellitus ("T2DM") animals were fasted overnight and on the following day they were given an intraperitoneal injection (i.p.) of 50 mg/kg of STZ in freshly prepared citrate buffer (pH 4) for three constitutive days to induce hypercalcemia. The animals were left for 5 days, then fasting blood glucose levels were measured with a glucometer.

Blood was drawn from each animal's tail vein (while the animal is under anesthesia). Rats with blood glucose levels above 200 mg/dL was considered diabetic. Diabetic rats were anesthetized using ether and square diabetic wounds (2.25 $cm^2$ in area) were induced on the dorsal position of rats after shaving their skin hair. The wounds were washed and cleaned by an ethanol solution (70%, v/v). Starting a day after surgery, animals were randomly categorized into five groups (n=8).

Group 1 (Control): rats were untreated and their wounds were left uncovered for 17 days. The wound diameter was recorded every four days.

Group 2 (Saline): rats were treated with saline as another control. The saline was placed in pure cotton, the wet cotton was affixed to the wound site with a bandage, and the cotton was replaced with fresh saline daily for a period of 17 days. The wound diameter was recorded every four days.

Group 3 (Commercial Diabetic Wound Dressing): rats were treated with a commercial bandage that was tied to the wound site for a period of 17 days. The wound diameter was recorded every four days.

Group 4 (Gum Olibanum Nanofibers): rats were treated with gum olibanum nanofibers, the gum olibanum nanofibers were affixed to the wound site with a bandage, and the gum olibanum nanofibers were replaced with fresh gum olibanum nanofibers daily for a period of 17 days. The wound diameter was recorded every four days.

Group 5 (Gum Olibanum/*Acacia nilotica* Composite Nanofibers): rats were treated with gum olibanum and *Acacia nilotica* composite nanofibers. The nanofibers were affixed to the wound site with a bandage, and the nanofibers were replaced with fresh nanofibers daily for a period of 17 days. The wound diameter was recorded every four days.

Finally, wounds of all animals in all Groups 1-5 were photographed on days 0, 3, 7, and 14 and the wound areas were measured using Image J software.

At the end of the experiment and after fasting, the animals were anesthetized, and blood was collected in two different tubes, (one with EDTA and another without anticoagulant for serum separation). These blood samples were centrifuged at 3000 rpm for 20 minutes using a refrigerated centrifuge at 4° C. to separate the serum. The pancreas, liver, and kidneys were collected immediately, cut into small pieces, fixed in 10% formalin, and subjected to a histological processes.

Figure 2:
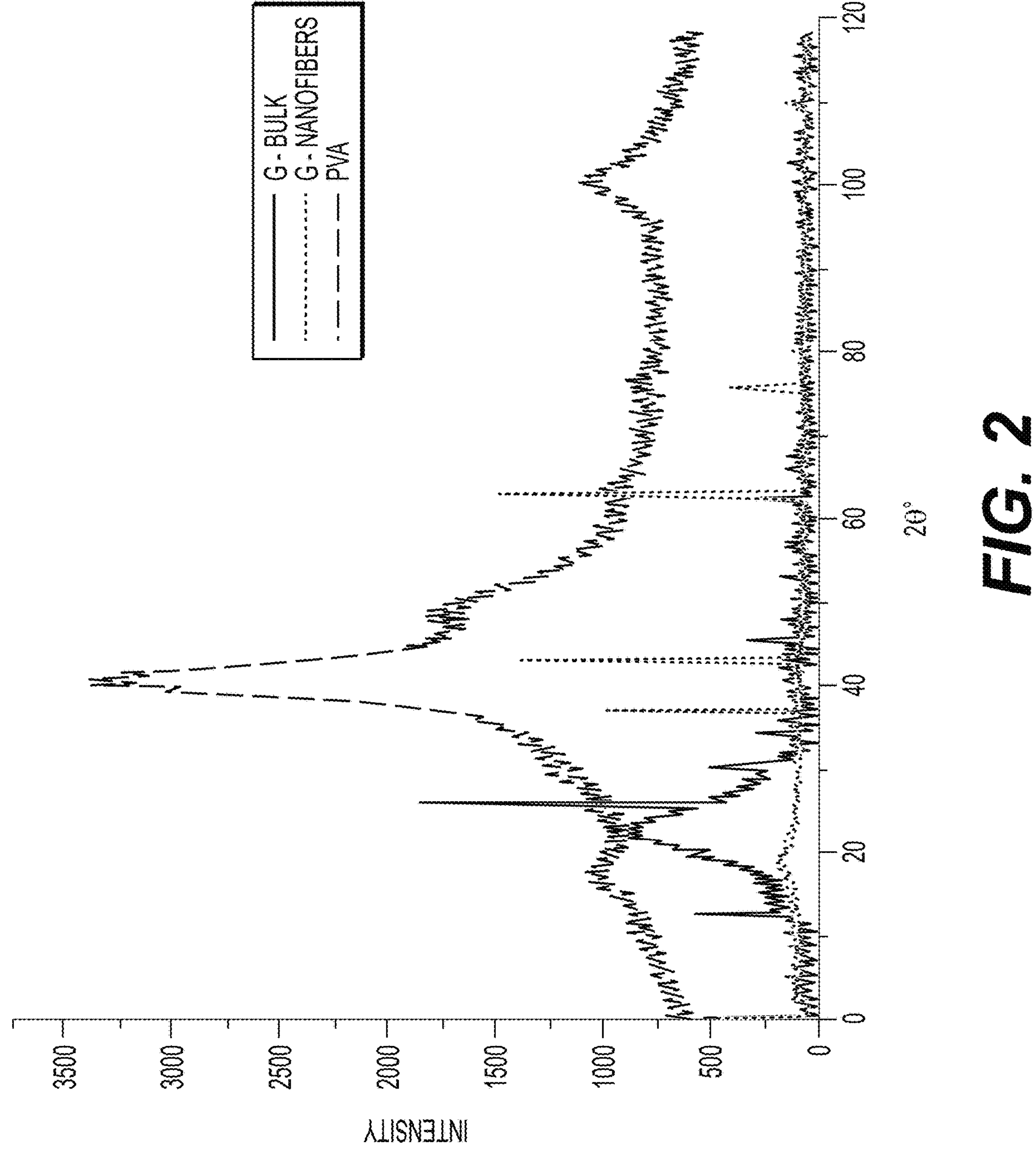
FIG. 2 depicts the XRD diffraction patterns of a sample of raw *Acacia nilotica* ("G-bulk"), a sample of gum olibanum nanofibers loaded with *Acacia nilotica* nanoparticles ("G-nanofibers"), and PVA.

XRD analysis results (see FIG. 1 and FIG. 2) indicate a significant difference in the structural characteristics of the materials before and after nanofiber fabrication. The wide spectra observed for PVA and gum olibanum suggest that these materials are predominantly amorphous, characterized by a disordered molecular arrangement with no long-range periodic structure. In contrast, the sharp spectra exhibited by the nanofibers indicates the presence of crystalline regions, implying that the nanofiber fabrication process, using electrospinning, has induced partial crystallinity.

Figure 3:
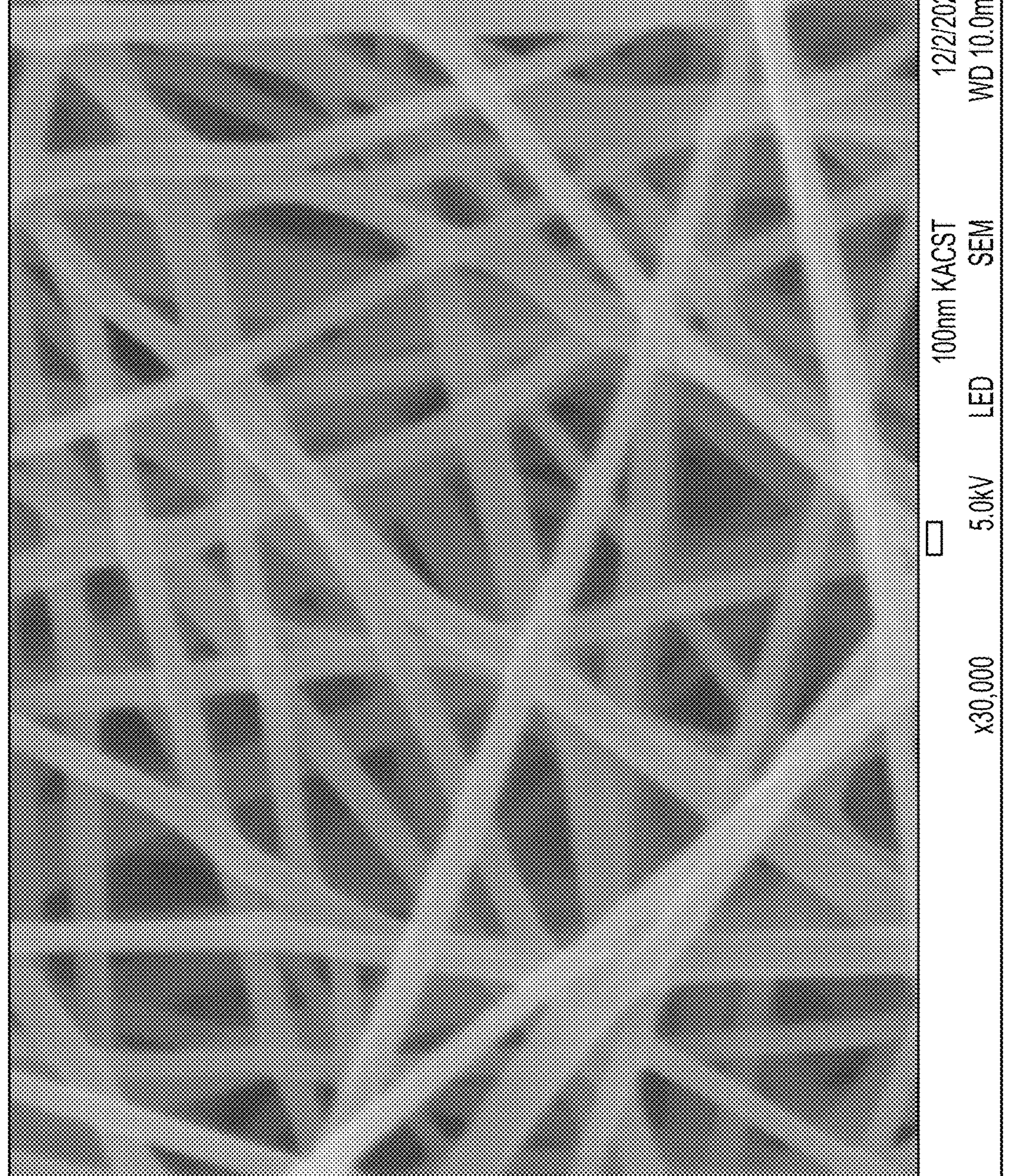
FIG. 3 depicts a scanning electron micrograph of the synthesized Gum olibanum nanofibers.
Figure 4:
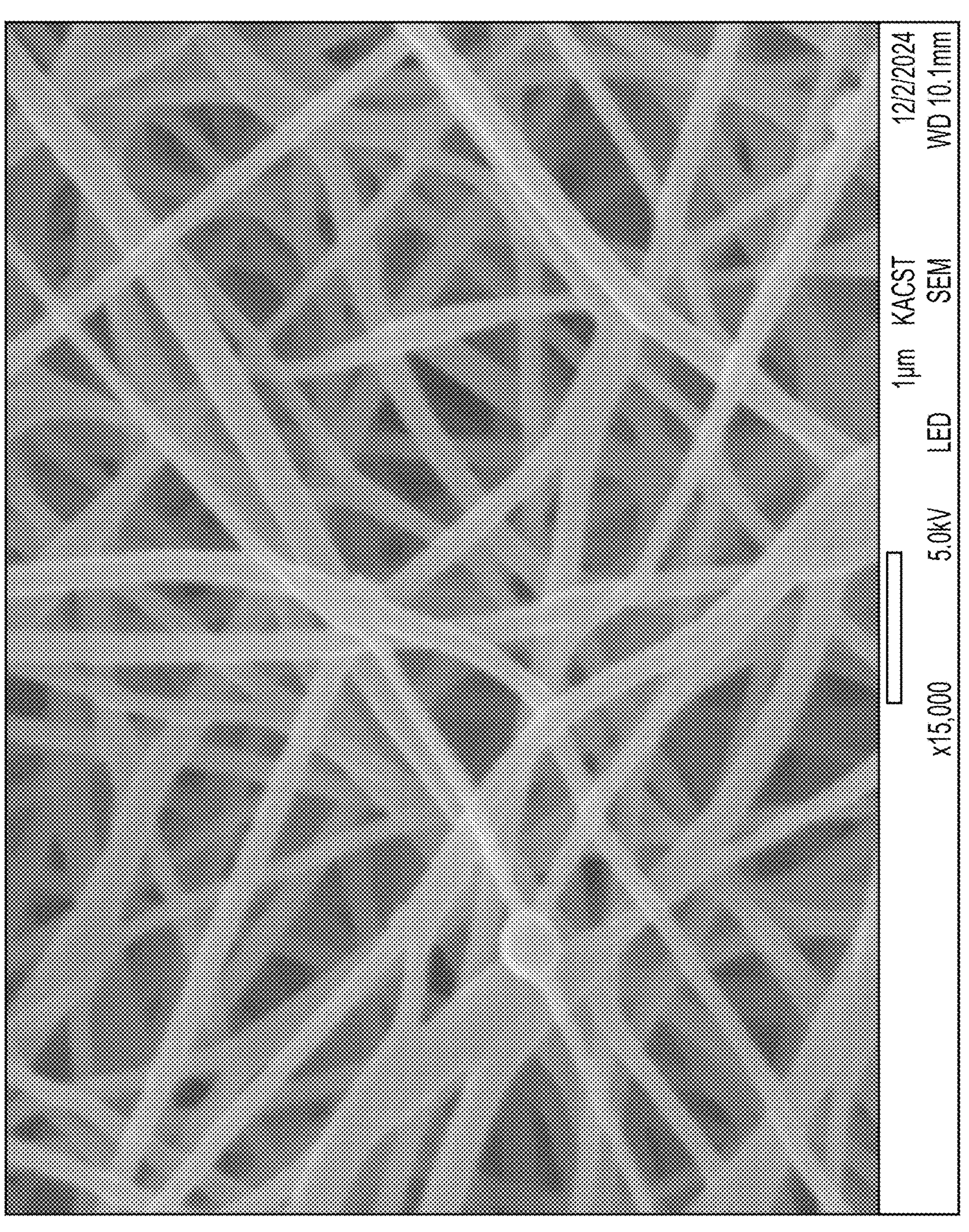
FIG. 4 depicts a scanning electron micrograph of the synthesized Gum olibanum nanofibers loaded with *Acacia nilotica* nanoparticles.
Figure 5:
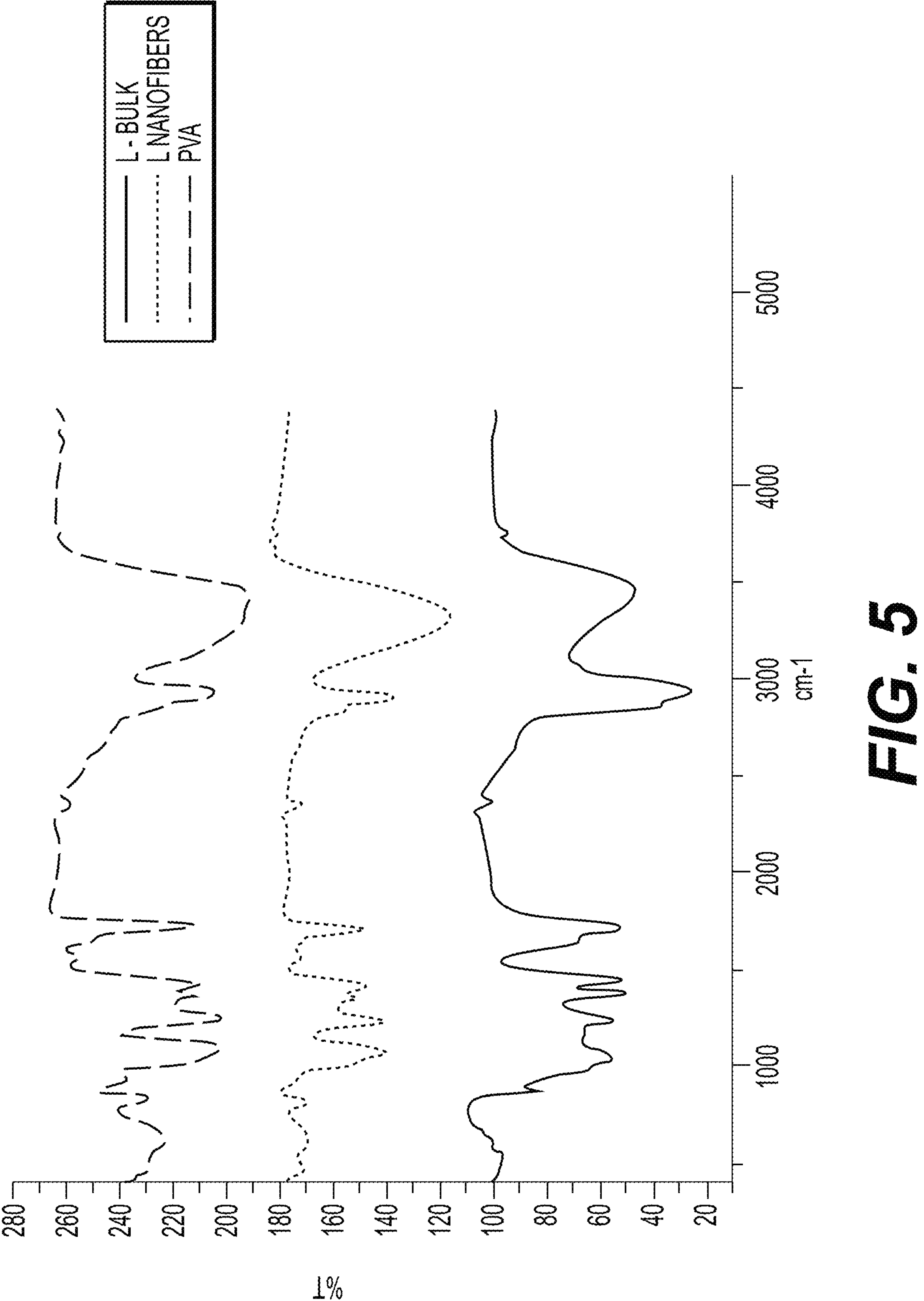
FIG. 5 depicts the Fourier transform infrared spectra of a sample of raw Gum Olibanum ("L-bulk"), a sample of gum olibanum nanofibers ("L-nanofibers"), and PVA.
Figure 6:
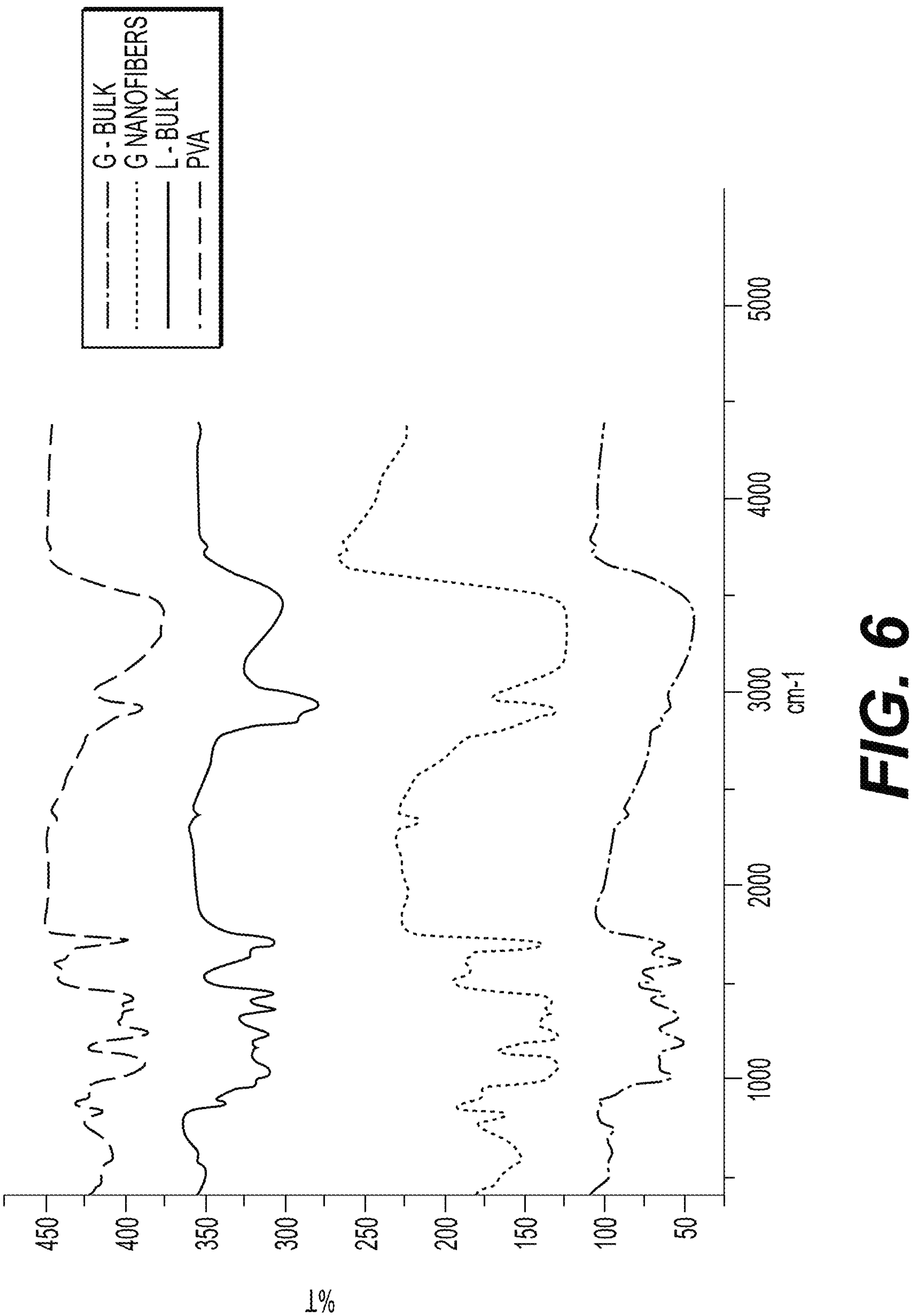
FIG. 6 depicts the Fourier transform infrared spectra of a sample of raw *Acacia nilotica* ("G-bulk"), a sample of gum olibanum nanofibers loaded with *Acacia nilotica* nanoparticles ("G-nanofibers"), and PVA.
Figure 7:
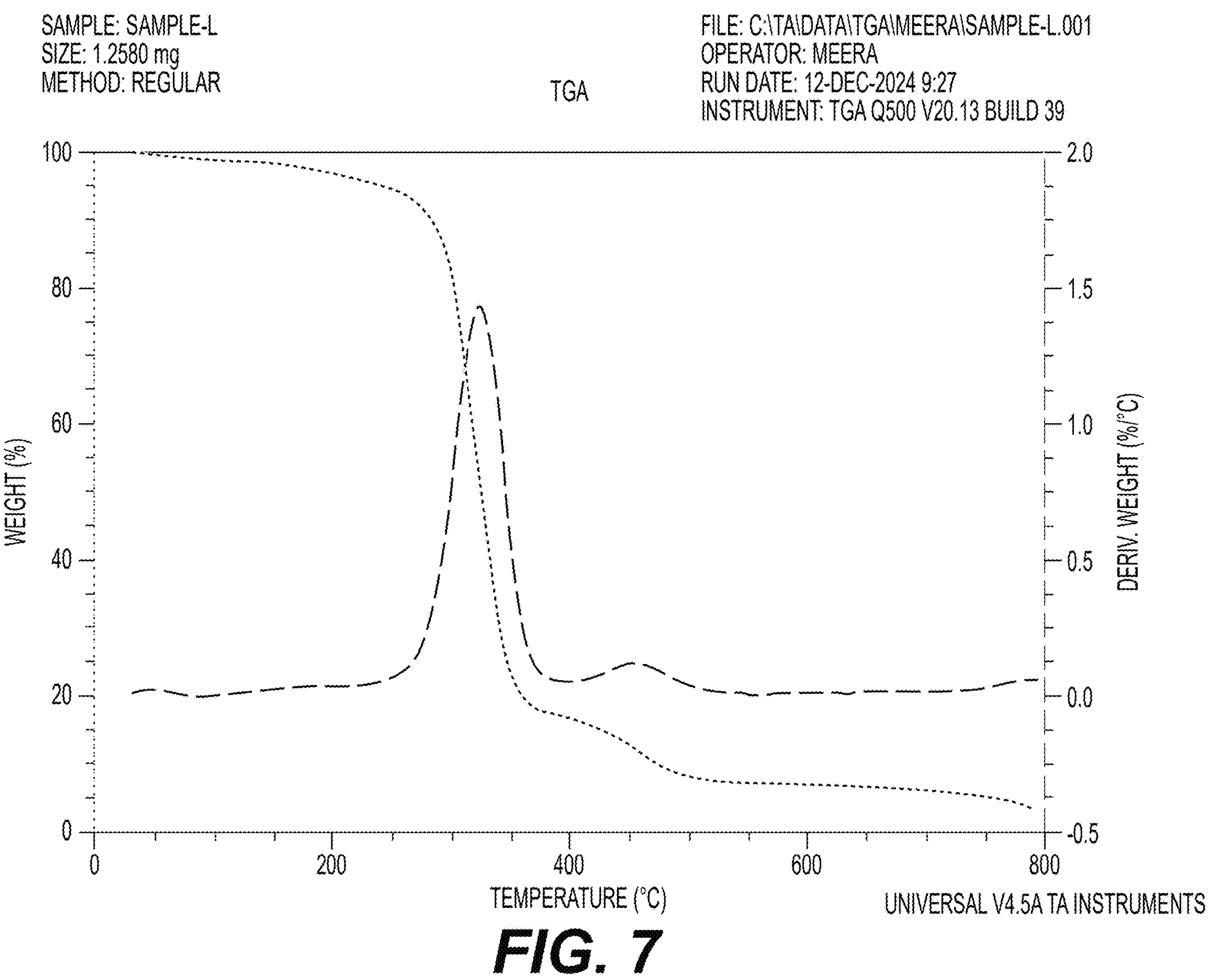
FIG. 7 depicts the thermal characterization analysis of gum olibanum nanofibers.

The morphology and diameter of the synthesized nanofibers were observed via scanning electron microscopy (SEM). The morphology of the synthesized nanofibers is depicted in FIG. 3 and FIG. 4.

Figure 11:
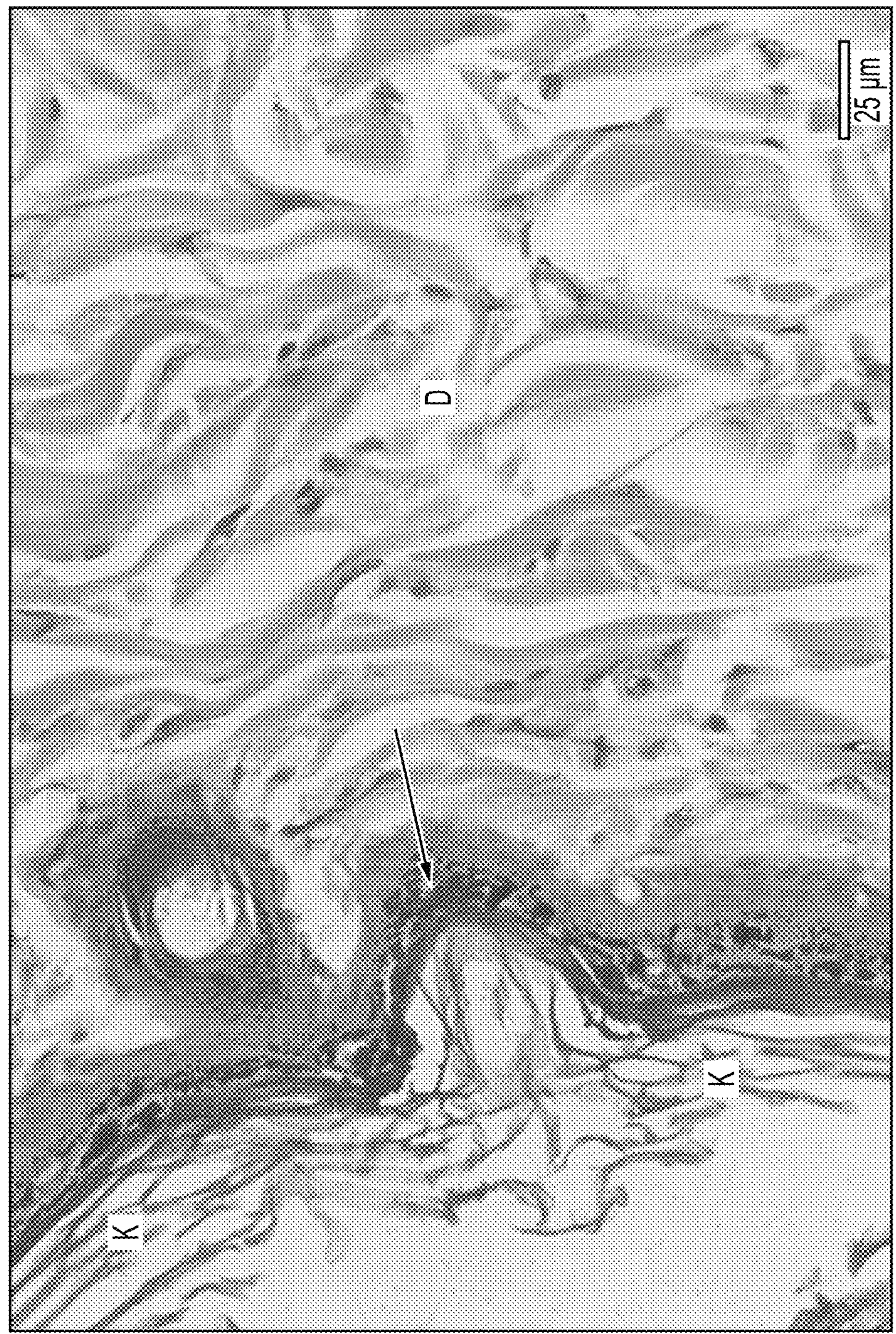
FIG. 11 depicts a photomicrograph of control skin showing normal skin with a thin layer of epidermis, granulosum (arrow), keratinized layers (K), and dermis (D) at 400×.
Figure 12:
FIG. 12 depicts a photomicrograph of an untreated wound without epidermis covered with edema (E), and showing an accumulation of infiltrative cells (circle) at 400×.
Figure 13:
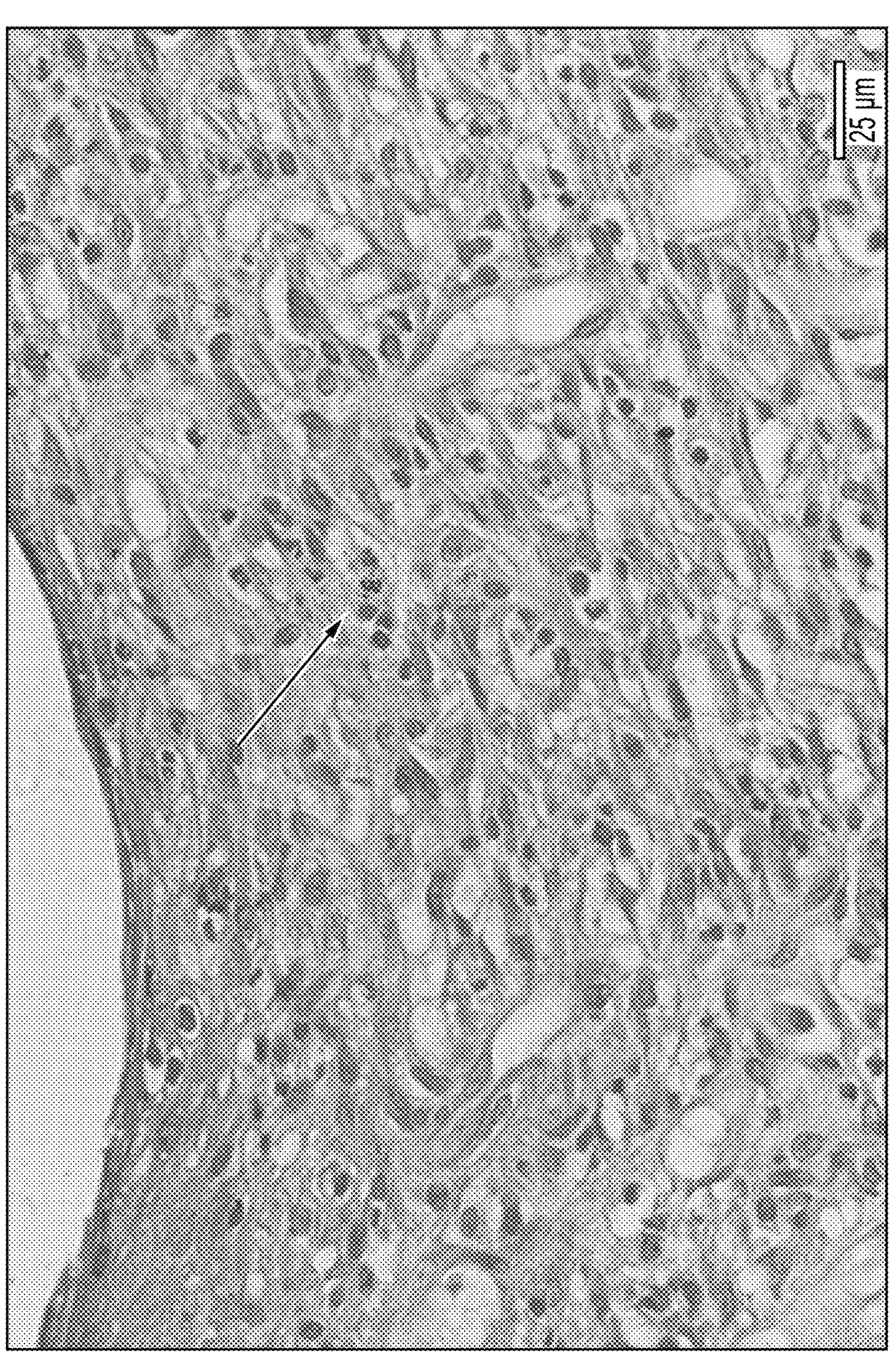
FIG. 13 depicts a photomicrograph of a wound covered with a commercial bandage revealing no epidermis, and dermis filled with scattered infiltrative cells (arrow) at 400λ.
Figure 14:
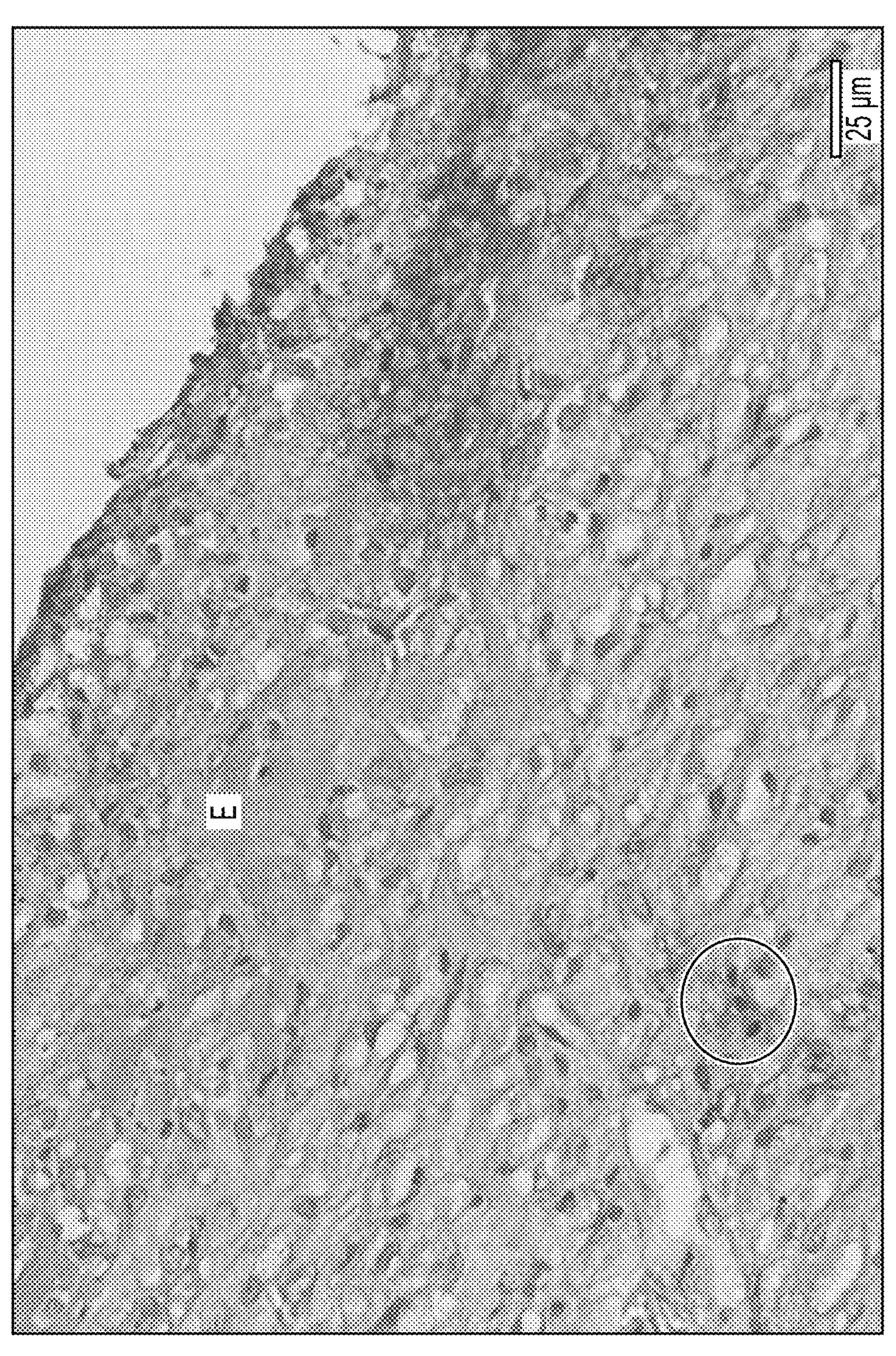
FIG. 14 depicts a photomicrograph of a wound treated with PVA/gum olibanum/*Acacia nilotica* nanofibers exhibiting no epidermis, edema (E), and infiltrative cells (circle) at 400×.
Figure 15:
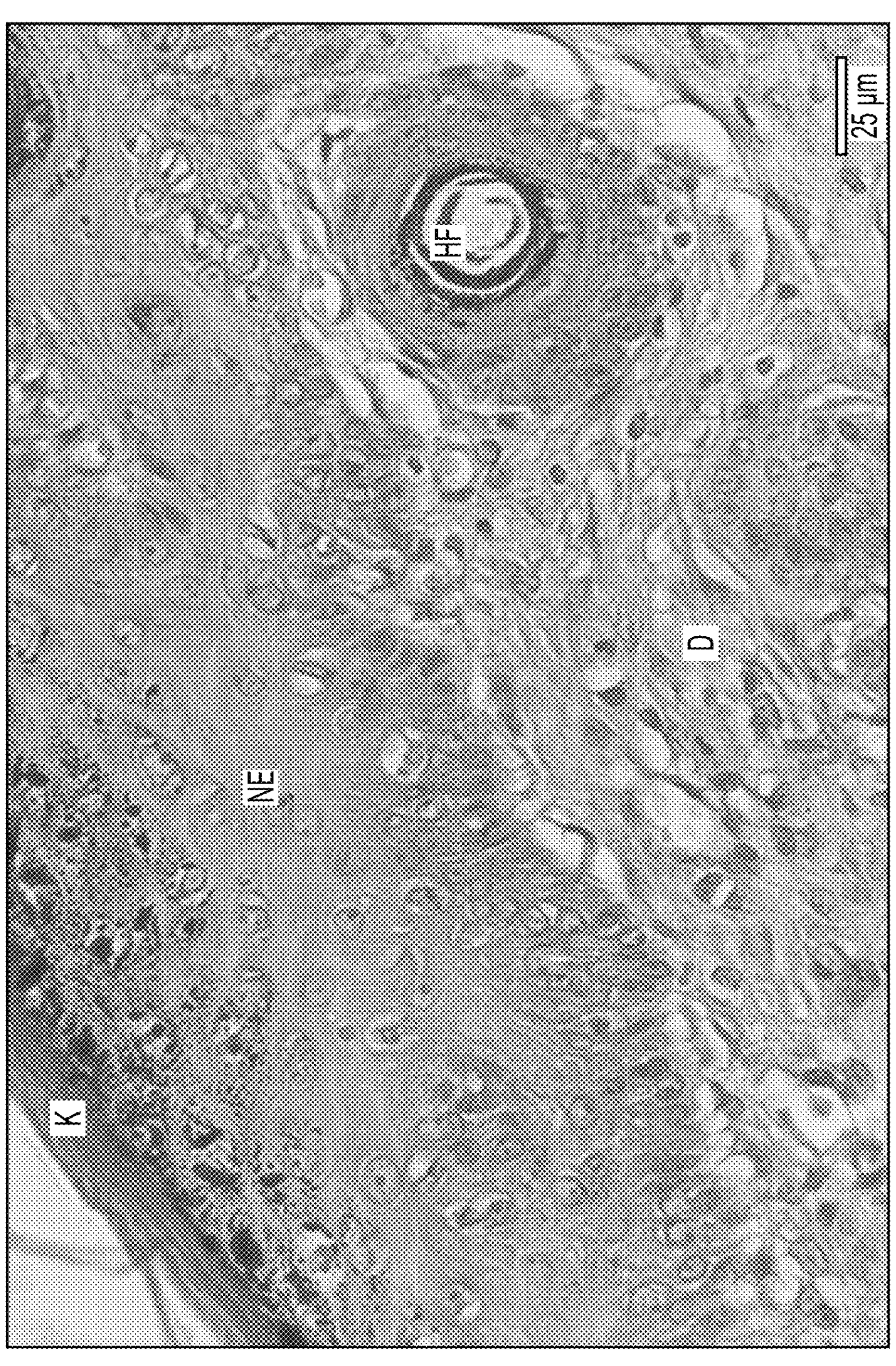
FIG. 15 depicts a photomicrograph of a wound treated with PVA/gum olibanum nanofibers revealing new epidermis (NE), new keratinized layer (K), dermis (D), and a fair follicle (HF) at 400×.
Figure 16:
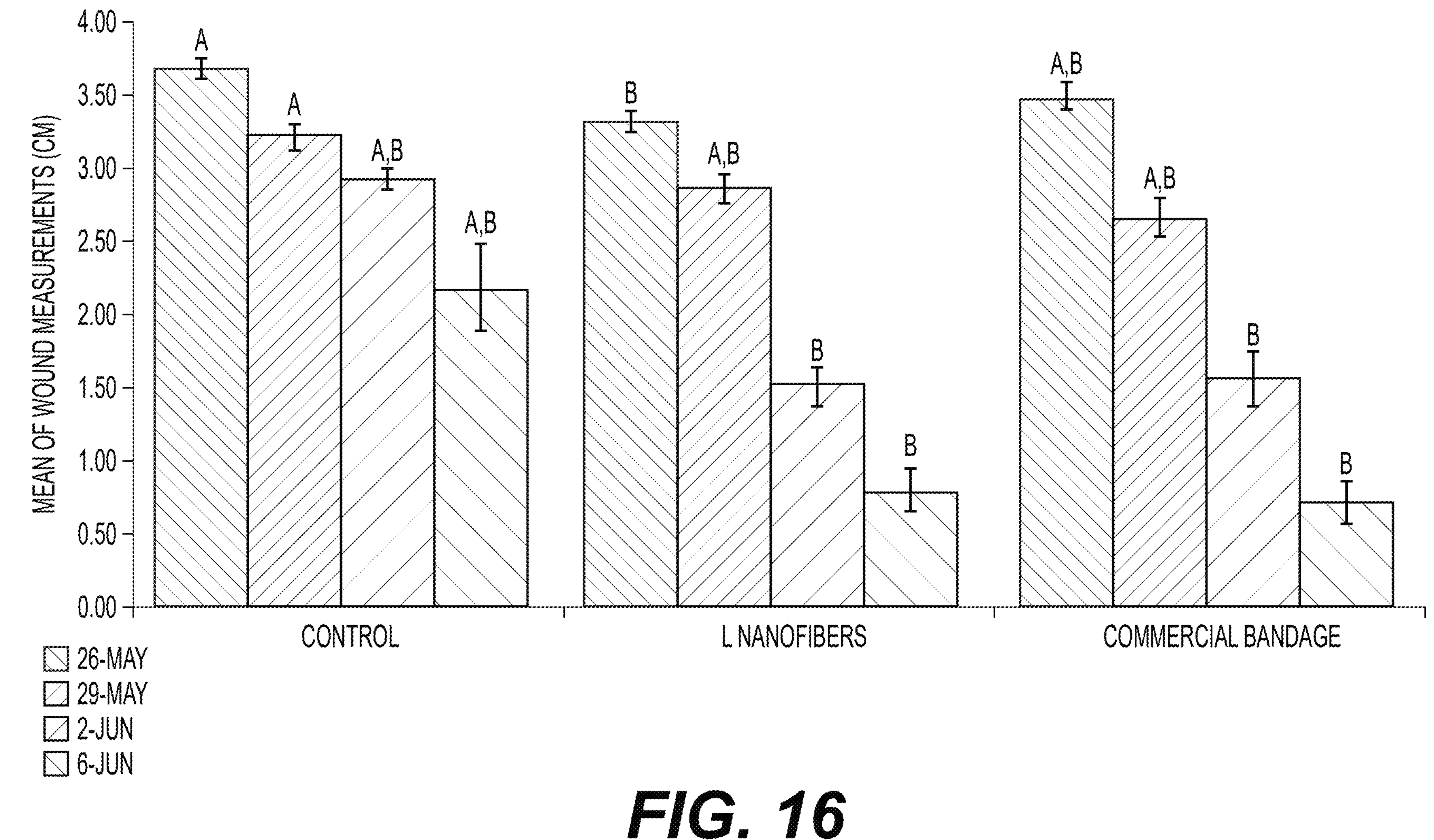
FIG. 16 depicts a graph illustrating wound size measurement after treatment with nothing ("control"), gum olibanum nanofibers ("L-nanofibers"), or a commercial bandage.
Figure 17:
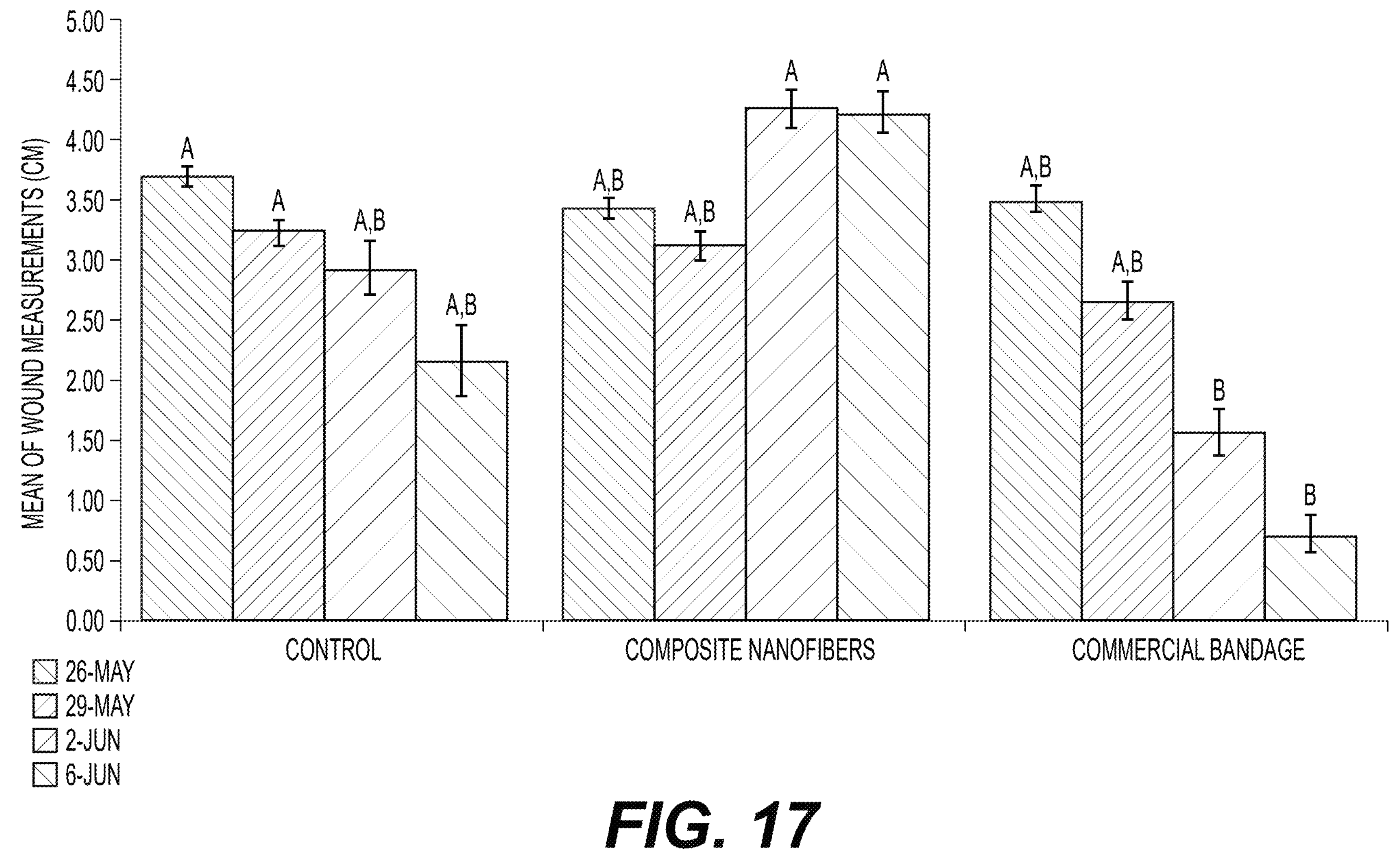
FIG. 17 depicts a graph illustrating wound size measurement after treatment with nothing (control), gum olibanum nanofibers loaded with *Acacia nilotica* nanoparticles ("composite nanofibers"), or a commercial bandage.
Figure 18:
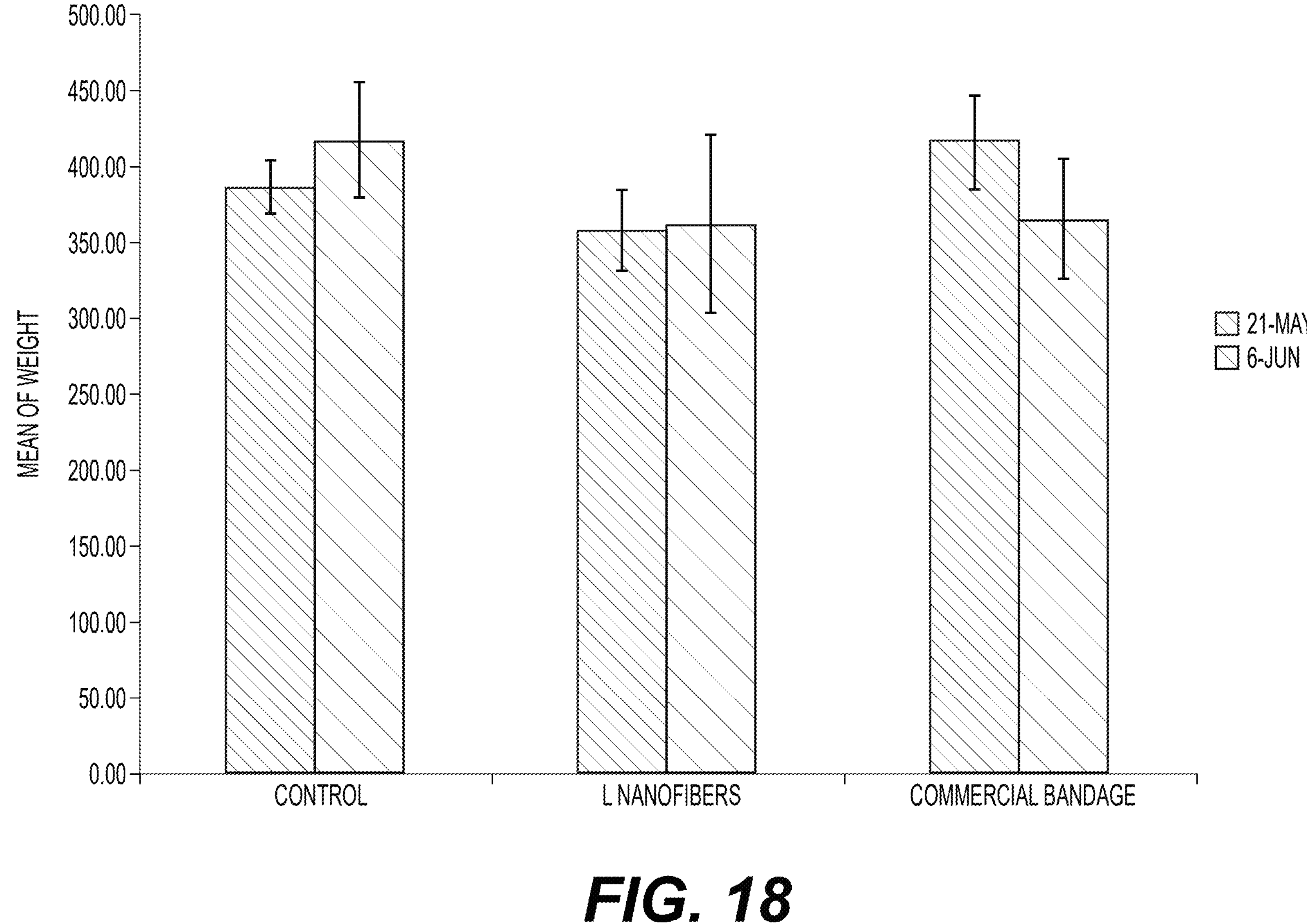
FIG. 18 depicts a graph illustrating weight measurement after treatment with nothing ("control"), gum olibanum nanofibers ("L-nanofibers"), or a commercial bandage.
Figure 19:
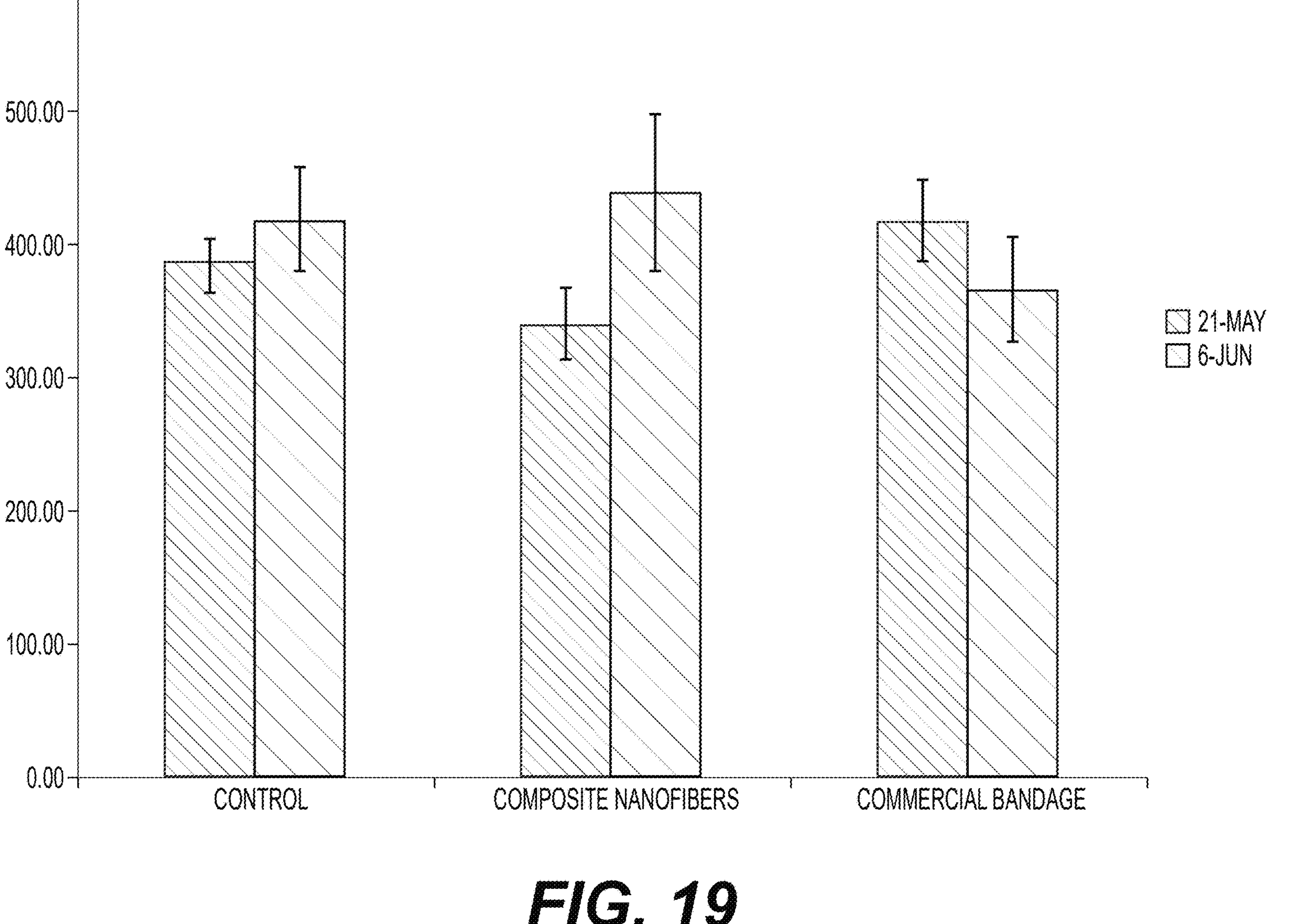
FIG. 19 depicts a graph illustrating weight measurement after treatment with nothing ("control"), gum olibanum nanofibers loaded with *Acacia nilotica* nanoparticles ("composite nanofibers"), or a commercial bandage.

The control skin showed a normal appearance, with a thin layer of epidermis covered by layers of keratin and a normal dermis containing old collagen (FIG. 11). The untreated wound exhibited an absence of the epidermis, edema, and an accumulation of infiltrative cells within the dermis (FIG. 12). Furthermore, the wound covered with commercial bandage showed no epithelial layer, while the dermis contained new collagen and infiltrative cells (FIG. 13). Additionally, the wound of animals treated with the synthesized PVA/gum olibanum nanofibers loaded with *Acacia nilotica* nanoparticles revealed no epidermis, along with the presence of edema and infiltrative cells (FIG. 14). Although the nanofiber treatments may have influenced collagen formation or other aspects of healing, their effectiveness in fully resolving the wound appears limited. This limitation could potentially be overcome by extending the treatment duration or exploring combination therapies. Furthermore, wound of animals treated with PVA/gum olibanum nanofibers showed more wound cure as thick newborn epithelia covered with keratin layers, dermis showed some infiltrative cells and new collagen (FIG. 15).

Notably, as illustrated in FIGS. 16-19, the gum olibanum nanofibers loaded with *Acacia nilotica* nanoparticles exhibited a less pronounced reduction in wound size compared to treatment with gum olibanum nanofibers alone. However, this observation does not necessarily indicate inferior performance. Rather, it reflects the distinct biological response and healing dynamics induced by the composite formulation during the experimental period (17 days).

As shown in the histological image (FIG. 14), treatment with the composite nanofibers (gum olibanum nanofibers loaded with *Acacia nilotica* nanoparticles) resulted in the presence of edema and inflammatory cell infiltration. This suggests that the phenolic compounds from *Acacia nilotica* triggered an initial inflammatory phase—a normal and essential stage in wound healing that activates immune cells to clean the wound site before tissue remodeling begins. In contrast, animals treated with gum olibanum nanofibers alone (FIG. 15) displayed the formation of new epidermis and keratinized layers, indicating a more advanced stage of wound repair within the same timeframe.

Figure 8:
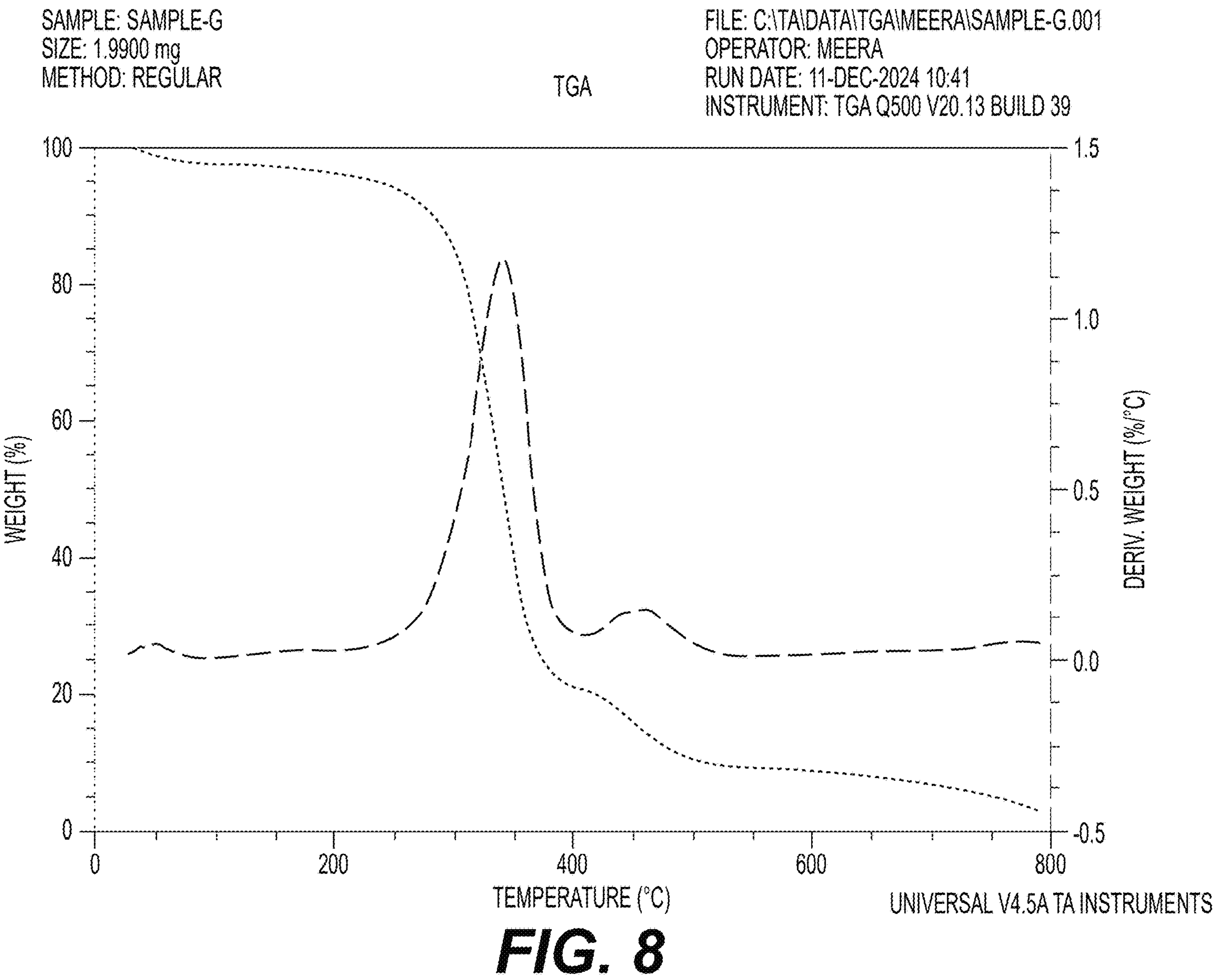
FIG. 8 depicts the thermal characterization analysis of gum olibanum nanofibers loaded with *Acacia nilotica* nanoparticles.

Although the wound contraction was lower, the composite nanofibers possess several biological and functional advantages demonstrated in this study:

a. Controlled and sustained drug release: As confirmed by the drug-release kinetics, the composite nanofibers provided a prolonged release of bioactive compounds, enhancing long-term therapeutic efficacy.

b. Antimicrobial and antioxidant properties: *Acacia nilotica* is rich in polyphenols and flavonoids, which contribute to microbial inhibition, oxidative stress reduction, and modulation of chronic inflammation-crucial factors in diabetic wound healing.

c. Potential for delayed but enhanced collagen formation: The synergistic interaction between *Acacia nilotica* and gum olibanum may stimulate collagen deposition and tissue regeneration during extended treatment periods, which may not be fully captured within the 17-day study window.

d. Improved thermal and structural stability: Thermogravimetric analysis (FIG. 8) confirmed that the composite nanofibers possess higher thermal stability and integrity, making them more suitable for biomedical applications requiring sterilization or sustained use.

It is to be understood that the gum olibanum nanofibers for drug release and wound healing applications is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of making gum olibanum nanofibers, the method comprising:

obtaining a quantity of gum olibanum;

adding the quantity of gum olibanum to acetic acid to obtain a first mixture;

mixing the first mixture;

adding water to the first mixture to obtain a second mixture;

continuously stirring and heating the second mixture at a speed of about 500-1000 rpm and at a temperature of about 85-90° C. until a clear, milky solution forms;

preparing an about 10 wt % aqueous solution of polyvinyl alcohol;

combining the clear, milky solution and the about 10 wt % aqueous solution of polyvinyl alcohol in an equal volume ratio to obtain a third mixture;

stirring the third mixture at a speed of about 100 rpm for about 5 hours to ensure thorough mixing and then resting the third mixture at room temperature for about 24 hours; and electrospinning the third mixture to produce the gum olibanum nanofibers.

2. The method of claim 1, wherein the about 10 wt % aqueous solution of polyvinyl alcohol is prepared by stirring a mixture of polyvinyl alcohol and water for about 10-12 hours at about 85-90° C.

3. The method of claim 1, wherein the quantity of gum olibanum is about 15 g.

4. The method of claim 3, wherein the quantity of gum olibanum is added to about 5 mL of acetic acid.

5. The method of claim 1, comprising adding about 100 ml of water to the first mixture to obtain the second mixture.

6. The method of claim 1, wherein the quantity of gum olibanum is obtained from a *Boswellia sacra* tree.

7. The method of claim 1, wherein electrospinning the third mixture comprises:

filling a syringe with the third mixture and attaching the syringe to an electrospinning machine;

applying a voltage of about 15 kV with a distance of about 15 cm maintained between the collector and the syringe tip;

collecting the gum olibanum nanofibers on the collector of the electrospinning machine; and drying the gum olibanum nanofibers in an oven at about 120° C. for about 6 hours to remove any residual solvent.

8. The method of claim 1, further comprising loading the gum olibanum nanofibers with a drug.

9. The method of claim 1, comprising:

obtaining *Acacia nilotica* plant material;

washing, air-drying, and grinding the *Acacia nilotica* plant material to obtain ground *Acacia nilotica* plant material;

sieving the ground *Acacia nilotica* plant material to obtain powdered *Acacia nilotica* plant material;

dissolving the powdered *Acacia nilotica* plant material in methanol to obtain an aqueous solution of *Acacia nilotica;* spraying the aqueous solution of *Acacia nilotica* dropwise into boiling water under a first set of ultrasonic conditions to obtain a first solution;

stirring the first solution at a controlled temperature of about 30° C. to about 35° C. to form *Acacia nilotica* nanoparticles within the first solution;

adding the first solution comprising *Acacia nilotica* nanoparticles to the gum olibanum nanofibers under a second set of ultrasonic conditions to obtain a second solution; and electrospinning the second solution to produce gum olibanum nanofibers loaded with *Acacia nilotica* nanoparticles.

10. The method of claim 9, comprising obtaining about 20 grams of the *Acacia nilotica* plant material.

11. The method of claim 9, comprising dissolving about 0.5 g of the powdered *Acacia nilotica* plant material in about 10 mL of the methanol to obtain the aqueous solitons of *Acacia nilotica.*

12. The method of claim 11, comprising spraying the aqueous solution of *Acacia nilotica* dropwise into about 50 mL of the boiling water at a flow rate of about 0.5 mL/min over about 5 minutes.

13. The method of claim 9, wherein the first set of ultrasonic conditions comprises about 750 W power and about 20 kHz frequency maintained for about 20-23 minutes; and wherein the second set of ultrasonic conditions comprises about 750 W power and about 20 KHz frequency maintained for about 3 hours.

14. The method of claim 9, wherein electrospinning the second solution comprises:

filling a syringe with the second solution;

attaching the syringe to an electrospinning machine; and applying a voltage of about 15 kV, with an about 15 cm distance maintained between a collector of the electrospinning machine and a tip of the syringe.

15. The method of claim 9, comprising drying the gum olibanum nanofibers loaded with *Acacia nilotica* nanoparticles in an oven at about 120° C. for about 6 hours to remove any residual solvent.

16. Gum olibanum nanofibers loaded with *Acacia nilotica* nanoparticles prepared according to the method of claim 9.

17. A method of treating a wound on a subject in need thereof, comprising administering the gum olibanum nanofibers loaded with *Acacia nilotica* nanoparticles of claim 16 to the wound on the subject in need thereof.

* * * * *